(12) United States Patent
Bammer et al.

(10) Patent No.: US 12,561,798 B2
(45) Date of Patent: Feb. 24, 2026

(54) CONCURRENT DISPLAY OF HEMODYNAMIC PARAMETERS AND DAMAGED BRAIN TISSUE

(71) Applicant: iSchemaView, Inc., Menlo Park, CA (US)

(72) Inventors: Roland Bammer, Carlton (AU); Matúš Straka, Winterthur (CH); Jürgen Endres, Heilsbronn (DE)

(73) Assignee: iSchemaView, Inc., Menlo Park, CA (US)

( * ) Notice: Subject to any disclaimer, the term of this patent is extended or adjusted under 35 U.S.C. 154(b) by 740 days.

(21) Appl. No.: 17/713,123

(22) Filed: Apr. 4, 2022

(65) Prior Publication Data

US 2023/0036757 A1 Feb. 2, 2023

Related U.S. Application Data

(63) Continuation-in-part of application No. 17/387,965, filed on Jul. 28, 2021, now Pat. No. 11,295,448.

(51) Int. Cl.
*G06T 7/00* (2017.01)
*A61B 6/00* (2024.01)

(52) U.S. Cl.
CPC ............ *G06T 7/0012* (2013.01); *A61B 6/481* (2013.01); *A61B 6/486* (2013.01); (Continued)

(58) Field of Classification Search
CPC ..... G06T 7/0014; G06T 7/337; G06T 11/008; G06T 2207/10081; G06T 2207/20081; (Continued)

(56) References Cited

U.S. PATENT DOCUMENTS

| 5,807,270 | A | 9/1998 | Williams |
| 7,338,447 | B2 | 3/2008 | Phillips |

(Continued)

FOREIGN PATENT DOCUMENTS

| AU | 2005212310 A1 | 8/2005 |
| CA | 2077760 C | 1/2001 |

(Continued)

OTHER PUBLICATIONS

U.S. Appl. No. 17/387,965 U.S. Pat. No. 11,295,448, filed Jul. 28, 2021, Concurrent Display of Hemodynamic Parameters and Damaged Brain Tissue.

(Continued)

*Primary Examiner* — Shefali D Goradia
(74) *Attorney, Agent, or Firm* — Schwegman Lundberg & Woessner, P.A.

(57) ABSTRACT

Images can be generated with overlays indicating an amount of brain tissue damage based on the disruption of blood supply. Imaging data can be analyzed to determine perfusion parameters with respect to regions of the brain of an individual. The thresholds for the perfusion parameters with respect to the presence of damaged brain tissue can be based on a period of time elapsed since the onset of a biological condition disrupting blood flow to one or more regions of the brain of the individual. The imaging data can also be analyzed to determine measures of hypodensity with respect to regions of the brain of the individual. A likelihood of the measures of hypodensity corresponding to damaged brain tissue can also be determined based on the period of time elapsed since the onset of the biological condition.

20 Claims, 11 Drawing Sheets

(52) U.S. Cl.
CPC .............. *G06T 2207/10081* (2013.01); *G06T 2207/30016* (2013.01); *G06T 2207/30104* (2013.01)

(58) Field of Classification Search
CPC . G06T 2207/20084; G06T 2207/30016; G06T 2207/30104; G06T 2211/404; A61B 6/032; A61B 6/501; A61B 6/504; A61B 6/507
See application file for complete search history.

(56) References Cited

U.S. PATENT DOCUMENTS

| | | | |
|---|---|---|---|
| 8,467,587 | B2 | 6/2013 | Buerger et al. |
| 8,615,116 | B2 | 12/2013 | Lardo et al. |
| 11,295,448 | B1 | 4/2022 | Bammer et al. |
| 2008/0319302 | A1 | 12/2008 | Meyer et al. |
| 2011/0257519 | A1 | 10/2011 | Bj et al. |
| 2013/0012813 | A1 | 1/2013 | Sakaguchi |
| 2014/0221235 | A1 | 8/2014 | Barr |
| 2015/0003706 | A1 | 1/2015 | Eftestøl et al. |
| 2016/0066861 | A1 | 3/2016 | Taylor |
| 2016/0180042 | A1 | 6/2016 | Menon et al. |
| 2017/0265829 | A1* | 9/2017 | Adam .................... A61B 6/501 |

FOREIGN PATENT DOCUMENTS

| | | | | |
|---|---|---|---|---|
| JP | 2024527975 | 7/2024 | | |
| WO | WO-2018217658 | A1 * | 11/2018 | ............. A61B 5/055 |
| WO | WO-2021179078 | A1 * | 9/2021 | ............. A61B 6/032 |
| WO | 2023010089 | | 2/2023 | |
| WO | WO-2023009999 | A1 * | 2/2023 | ........... A61B 5/0261 |

OTHER PUBLICATIONS

"European Application Serial No. 22850526.9, Extended European Search Report mailed Nov. 7, 2024", 10 pages.
Kawiorski, Michal M, "Good Clinical and Radiological Correlation from Standard Perfusion Computed Tomography Accurately Identifies Salvageable Tissue in Ischemic Stroke", Journal of Stroke and Cerebrovascular Diseases, Demos Publications, New York, NY, US, vol. 25, No. 5, (Feb. 5, 2016), pp. 1062-1069.
Vagal, Achala, "Automated CT perfusion imaging for acute ischemic stroke", Neurology, vol. 93, No. 20, (Nov. 12, 2019), pp. 888-898.
"International Application Serial No. PCT US2022 074272, International Search Report mailed Oct. 27, 2022", 2 pages.
"International Application Serial No. PCT US2022 074272, Written Opinion mailed Oct. 27, 2022", 8 pages.
"International Application Serial No. PCT US2022 074272, International Preliminary Report on Patentability mailed Feb. 8, 2024", 10 pages.
Ostergaard, "High resolution measurement of cerebral blood flow using intravascular tracer bolus passages. Part 1: Mathematical approach and statistical analysis", Magnetic resonance in medicine 36.5, [Online]. Retrieved from the Internet:URL: https: onlinelibrary.wiley.com doi abs 10.1002 mrm. 1910360510, (2015), 11 pages.
"U.S. Appl. No. 17/387,965, 312 Amendment filed Feb. 28, 2022", 11 pgs.
"U.S. Appl. No. 17/387,965, Notice of Allowance mailed Nov. 30, 2021", 11 pgs.
"U.S. Appl. No. 17/387,965, PTO Response to Rule 312 Communication mailed Mar. 7, 2022", 2 pgs.
Barbone, Giacomo E, et al., "Micro-imaging of brain cancer radiation therapy using phase-contrast computed tomography", International Journal of Radiation Oncology* Biology* Physics 101.4, (2018), 965-984.
"European Application Serial No. 22850526.9, Response filed May 22, 2025 to Extended European Search Report mailed Nov. 7, 2024", w English Claims, 9 pages.
"European Application Serial No. 22850526.9, Communication Pursuant to Article 94(3) EPC mailed Jul. 17, 2025", 5 pages.
"Japanese Application Serial No. 2024-504985, Voluntary Amendment filed Jul. 25, 2025", with English claims, 11 pages.
D'Esterre, Christopher D, "Time-Dependent Computed Tomographic Perfusion Thresholds for Patients With Acute Ischemic Stroke", Stroke, vol. 46, No. 12, XP055968647, US ISSN: 0039-2499, DOI: 10.1161 STROKEAHA.115.009250, (Dec. 1, 2015), 8 pages.

* cited by examiner

400

600

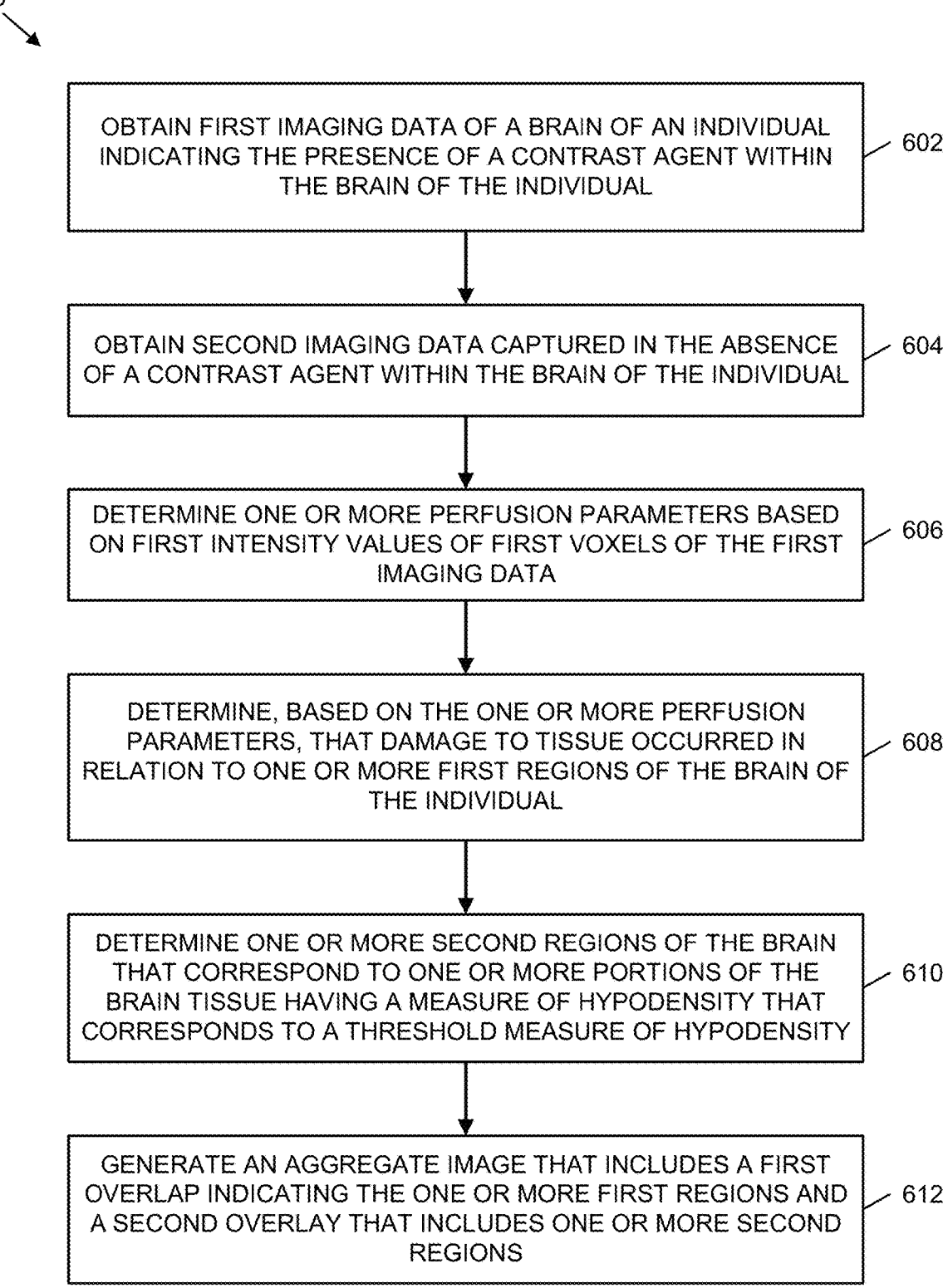

OBTAIN FIRST IMAGING DATA OF A BRAIN OF AN INDIVIDUAL INDICATING THE PRESENCE OF A CONTRAST AGENT WITHIN THE BRAIN OF THE INDIVIDUAL — 602

OBTAIN SECOND IMAGING DATA CAPTURED IN THE ABSENCE OF A CONTRAST AGENT WITHIN THE BRAIN OF THE INDIVIDUAL — 604

DETERMINE ONE OR MORE PERFUSION PARAMETERS BASED ON FIRST INTENSITY VALUES OF FIRST VOXELS OF THE FIRST IMAGING DATA — 606

DETERMINE, BASED ON THE ONE OR MORE PERFUSION PARAMETERS, THAT DAMAGE TO TISSUE OCCURRED IN RELATION TO ONE OR MORE FIRST REGIONS OF THE BRAIN OF THE INDIVIDUAL — 608

DETERMINE ONE OR MORE SECOND REGIONS OF THE BRAIN THAT CORRESPOND TO ONE OR MORE PORTIONS OF THE BRAIN TISSUE HAVING A MEASURE OF HYPODENSITY THAT CORRESPONDS TO A THRESHOLD MEASURE OF HYPODENSITY — 610

GENERATE AN AGGREGATE IMAGE THAT INCLUDES A FIRST OVERLAP INDICATING THE ONE OR MORE FIRST REGIONS AND A SECOND OVERLAY THAT INCLUDES ONE OR MORE SECOND REGIONS — 612

Figure 6

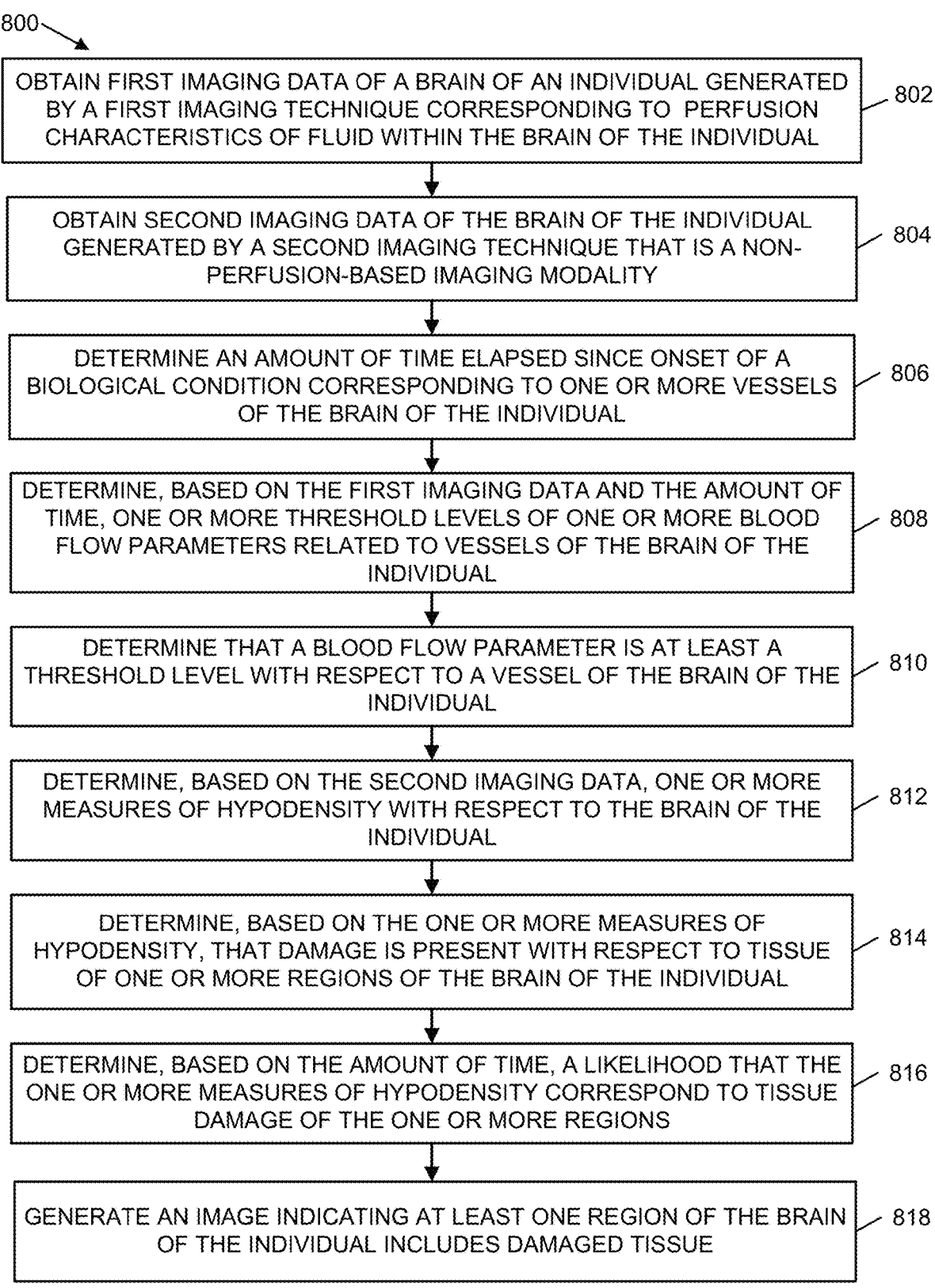

800

OBTAIN FIRST IMAGING DATA OF A BRAIN OF AN INDIVIDUAL GENERATED BY A FIRST IMAGING TECHNIQUE CORRESPONDING TO  PERFUSION CHARACTERISTICS OF FLUID WITHIN THE BRAIN OF THE INDIVIDUAL — 802

OBTAIN SECOND IMAGING DATA OF THE BRAIN OF THE INDIVIDUAL GENERATED BY A SECOND IMAGING TECHNIQUE THAT IS A NON-PERFUSION-BASED IMAGING MODALITY — 804

DETERMINE AN AMOUNT OF TIME ELAPSED SINCE ONSET OF A BIOLOGICAL CONDITION CORRESPONDING TO ONE OR MORE VESSELS OF THE BRAIN OF THE INDIVIDUAL — 806

DETERMINE, BASED ON THE FIRST IMAGING DATA AND THE AMOUNT OF TIME, ONE OR MORE THRESHOLD LEVELS OF ONE OR MORE BLOOD FLOW PARAMETERS RELATED TO VESSELS OF THE BRAIN OF THE INDIVIDUAL — 808

DETERMINE THAT A BLOOD FLOW PARAMETER IS AT LEAST A THRESHOLD LEVEL WITH RESPECT TO A VESSEL OF THE BRAIN OF THE INDIVIDUAL — 810

DETERMINE, BASED ON THE SECOND IMAGING DATA, ONE OR MORE MEASURES OF HYPODENSITY WITH RESPECT TO THE BRAIN OF THE INDIVIDUAL — 812

DETERMINE, BASED ON THE ONE OR MORE MEASURES OF HYPODENSITY, THAT DAMAGE IS PRESENT WITH RESPECT TO TISSUE OF ONE OR MORE REGIONS OF THE BRAIN OF THE INDIVIDUAL — 814

DETERMINE, BASED ON THE AMOUNT OF TIME, A LIKELIHOOD THAT THE ONE OR MORE MEASURES OF HYPODENSITY CORRESPOND TO TISSUE DAMAGE OF THE ONE OR MORE REGIONS — 816

GENERATE AN IMAGE INDICATING AT LEAST ONE REGION OF THE BRAIN OF THE INDIVIDUAL INCLUDES DAMAGED TISSUE — 818

CONCURRENT DISPLAY OF HEMODYNAMIC PARAMETERS AND DAMAGED BRAIN TISSUE

CROSS-REFERENCE TO RELATED APPLICATION

This application is a continuation-in-part of U.S. patent application Ser. No. 17/387,965, filed on Jul. 28, 2021, and entitled "CONCURRENT DISPLAY OF HEMODYNAMIC PARAMETERS AND DAMAGED BRAIN TISSUE," which is incorporated by reference herein in its entirety.

BACKGROUND

Damage can occur to tissue in the human body when blood flow is disrupted to the tissue. Decreased blood flow to tissue can have a number of causes, such as blood vessel blockage, rupture of blood vessels, constriction of blood vessels, or compression of blood vessels. The severity of the damage to the tissue can depend on the extent of the blood flow disruption to the tissue and the amount of time that blood flow to the tissue is disrupted. In situations where blood supply to tissue is inadequate for a prolonged period of time, the tissue may become infarcted. Infarcted tissue can result from the death of cells of the tissue due to the lack of blood supply.

BRIEF DESCRIPTION OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some implementations are illustrated by way of example, and not limitation.

FIG. 6 is a flowchart illustrating example operations of a process to determine an aggregate image based on image data generated by different imaging modalities and to generate overlays of the aggregate image indicating a potential amount of damage to brain tissue, according to one or more example implementations.

FIG. 8 is a flowchart illustrating example operations of a process to generate output images indicating damaged brain tissue based on onset of a biological condition corresponding to one or more vessels of brains of individuals, according to one or more example implementations.

DETAILED DESCRIPTION

Figure 1:
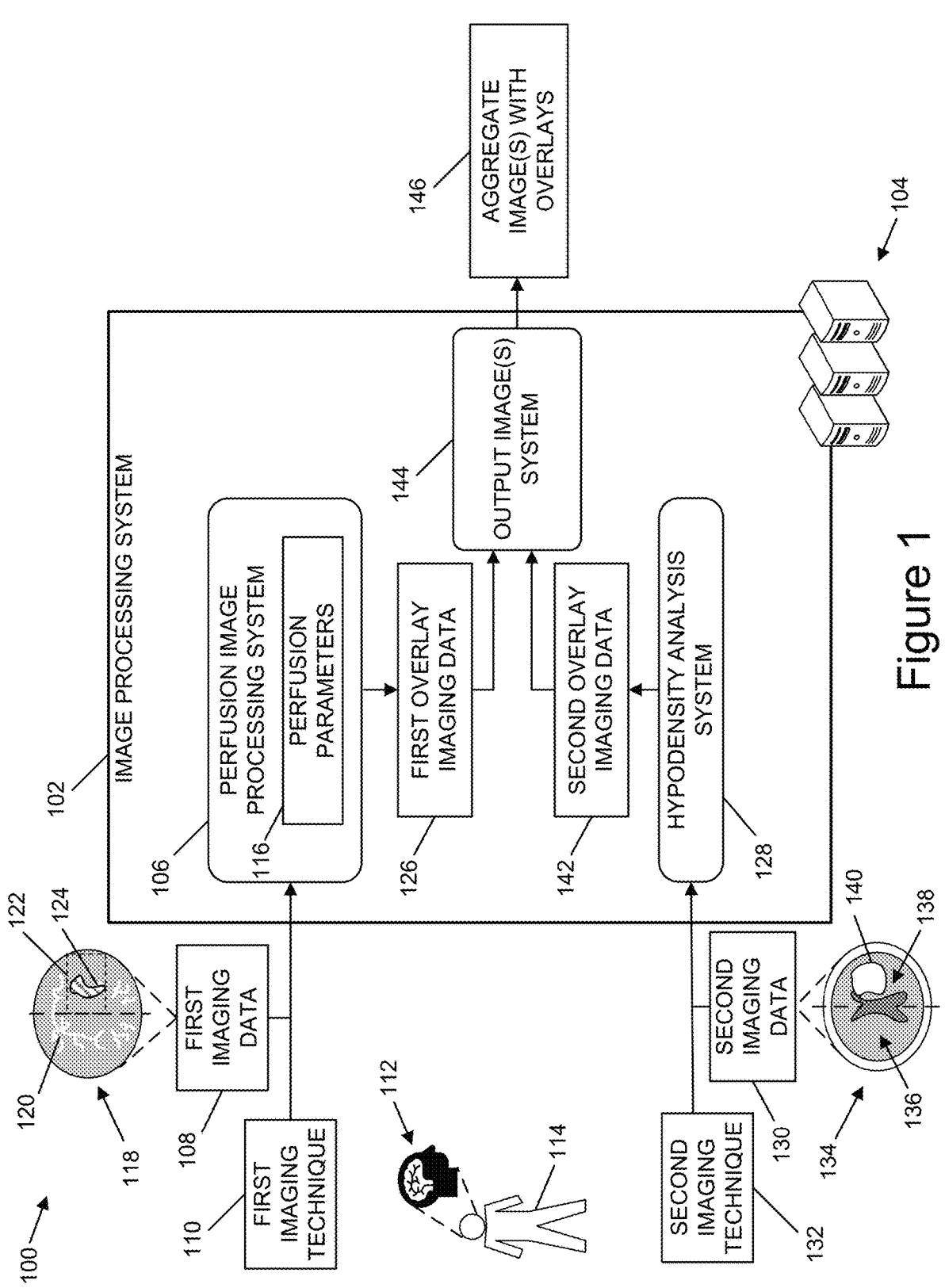
FIG. 1 is a diagrammatic representation of an example architecture for generating images that aggregate data from different imaging modalities and that include overlays indicating potential damage to brain tissue, according to one or more example implementations.

Various imaging techniques can be performed to determine an extent of damage and/or risk to tissue due to decreased blood flow to the tissue. In one or more examples, perfusion-based imaging techniques can be implemented to identify regions of the brain of an individual that experienced a decreased supply of blood. Another implementation would be the performing the assessment through a cerebral angiography. For example, computed tomography (CT) imaging techniques can be used to capture images of the brain of an individual. The images generated by the CT imaging techniques can be analyzed to determine regions of the brain of the individual that have been damaged are at high risk to undergo irreversible damage due to lack of blood supply to the regions. In various examples, a contrast agent can be delivered to the individual and CT images can be captured indicating the flow of the contrast agent through blood vessels that supply blood to the brain of the individual. When images are taken while the contrast is still in the arteries this is called a CT Angiography (CTA). CTA imaging techniques can include capturing images of vessels that carry blood to the brain and provide an indication of narrowing or blockage of vessels. Severe narrowing or blockage of vessels supplying blood to the brain can result in damage to tissue where the flow of blood is impaired or disrupted. Thus, in at least some instances, an amount of narrowing or blockage of one or more blood vessels can raise suspicion for a region of the brain that has sustained tissue damage or that can may sustain tissue damage in the future. When images are taken dynamically during the time that the contrast agent is passing through the large arteries, capillary bed, and draining veins with the intent to derive hemodynamic parameters such as blood flow or blood arrival time in tissue, the technique is called CT perfusion (CTP). The disruption of the flow of contrast agent to a region of the brain can indicate a lack of blood supply to the region of the brain that can result in damage to brain tissue in the region. In one or more examples, the contrast agent can include iodine or gadolinium that is disposed within a carrier solution. Perfusion-based magnetic resonance (MR) imaging techniques that implement a contrast agent can also be used to identify regions of the brain of the individual in which the supply of blood has been disrupted.

Additionally, non-contrast agent-based imaging techniques can be implemented to identify regions of a brain of an individual that may be damaged due to a lack of blood supply. To illustrate, diffusion-based MR imaging techniques can be used to determine portions of a brain of an individual where blood supply has been disrupted and that have consequently been damaged. In at least some examples, the damage to brain tissue may be irreversible. In one or more illustrative examples, diffusion-based MR imaging techniques can be implemented to identify brain tissue that has been damaged due to a lack of blood supply. Further, non-contrast CT imaging techniques can be used to determine regions of the brain tissue that have been damaged due to insufficient blood supply to the regions. In the hyperacute phase of an infarct, subtle intensity and morphologic changes on non-contrast CT head images can reveal areas of brain tissue that can no longer be salvaged. The non-contrast CT is typically a separate CT acquisition, but the information can be also derived from dynamic CT Perfusion scan phases that are taken before the contrast material arrives in the brain. The scan phases captured prior to the contrast agent entering the brain can be referred to as baseline time points. Baseline time points can also be derived from non-contrast CT images of the brain.

Determining an amount of tissue damage to the brain of an individual and how much more brain tissue can be in jeopardy if blood flow to the tissue cannot be restored can be used to determine treatment options for the individual. In various examples, reperfusion therapies can be implemented to restore blood supply to regions of the brain that have suffered a disruption. In various examples, an effectiveness of reperfusion therapies can be based on an extent of existing damage to brain tissue in response to a condition resulting in lack of blood flow to the brain tissue. In one or more examples, various interventions to restore blood flow to regions of the brain may be ineffective or cause additional damage to the individual based on an amount of existing tissue damage to the brain of the individual. Thus, since the safety and effectiveness of interventions to restore blood flow to brain tissue can be dependent on the amount of damage to the brain tissue, improvements in the accuracy of techniques used to determine the amount of damage to brain tissue cause by a disruption in the supply of blood is desired.

In existing imaging techniques, the amount of damage to brain tissue caused by a lack of supply of blood can be underestimated. For example, a region of the brain for which blood flow is disrupted from a first source of blood can be supplied with blood from a second source. However, in various scenarios, the blood supplied to the region from the second source may reach the region after damage has already occurred due to the disruption of blood supply from the first source. Thus, in situations where perfusion imaging is used to determine tissue damage to a region of the brain, images captured using perfusion imaging techniques can show that blood supply has been restored to the region despite preexisting damage to the brain tissue of the region. Since the images captured using perfusion imaging techniques can indicate reperfusion, a determination of tissue damage based on the images captured using the reperfusion imaging techniques may be underestimated. In these scenarios, treatment options provided to an individual may not be effective for the actual amount of brain tissue damage, but rather may be effective for the apparent amount of brain tissue damage indicated by the images captured using the perfusion-based imaging techniques. Accordingly, the treatments provided to an individual in these instances can be less effective than in situations where the treatment options provided to the individual correspond with the actual amount of brain tissue damage.

Perfusion imaging is used to infer in acute stroke patients that tissue is damaged if the blood flow in that region has substantially dropped. For example, damaged brain tissue can be determined in situations where the blood flow to the region in a first hemisphere of the brain is less than 30% of the value in a corresponding region of a second hemisphere of the brain. Empirically we see that such strong blood flow reductions are a good but not perfect predictor for permanently damaged brain tissue. However, the absence of these cerebral blood flow drops may not always be taken as a sign of undamaged brain tissue. For example, thrombolysis agents might have been given to dissolve the blood clot or the clot might have migrated more distally in the vessel and by doing so freed up segments that contained outlets (ostia) of branch vessels. That is, some regions can be at least partially reperfused. In such cases, perfusion-based imaging might not show a drop in blood flow for these regions as a result of the successful reperfusion of these regions. However, the underlying tissue in that region might be already irreversibly damaged. As the overall volume of irreversibly damaged tissue is an important factor to make decisions whether to treat a patient, knowing as precisely as possible the volume of tissue that cannot be salvaged is a key piece of knowledge. Therefore, one needs to include additional information to account for irreversibly damaged tissue that is not detectable in perfusion images. This is where the added information from non-contrast CT can be helpful. The combination of perfusion-based images and hypodensity values determined using non-contrast CT images gives a truer estimate of the infarct size than just one method alone.

The techniques, systems, processes, and methods described herein are directed to generating images that provide a more accurate indication of the amount of brain tissue damage based on disruption of blood supply than existing techniques. In one or more implementations, first imaging data can be generated by a first imaging technique and second imaging data can be generated by a second imaging technique. The first imaging technique can be a perfusion-based imaging technique. To illustrate, the first imaging technique can include CT-perfusion imaging. The second imaging technique can be a non-perfusion-based imaging technique. For example, the second imaging technique can include non-contrast CT imaging.

The voxel intensities of the first imaging data can be analyzed to determine a number of perfusion parameters that indicate the supply of blood to a number of regions of the brain of an individual. The number of perfusion parameters can be used to determine one or more first regions of brain tissue of the individual that has been damaged. The one or more first regions can be displayed as an overlay that is disposed on one or more images of the brain of the individual generated using the first imaging technique. In one or more examples, the perfusion parameters can indicate that the one or more first regions of the brain of the individual have undergone irreversible damage. Additionally, the perfusion parameters can indicate that there is at least a threshold probability of damage taking place with respect to the one or more first regions.

Additionally, voxel intensities of the second imaging data can be analyzed to determine one or more second regions of brain tissue of the individual that have been damaged. In one or more examples, the second imaging data can be analyzed to generate indicators of hypodensity related to regions of the brain of the individual. Hypodensity refers to a decrease in density of a region of brain tissue. The decrease in density of the region of brain tissue can be the result of water content in the region that is more than an amount of water content found in healthy brain tissue. In various examples, hypodensity can be an indicator of damaged brain tissue. In one or more examples, one or more regions of the brain having at least a threshold measure of hypodensity that corresponds to brain tissue damage can be indicated as an overlay disposed on one or more images of the brain of the individual generated using the second imaging technique. In one or more examples, the indicators of hypodensity can indicate that the one or more second regions of the brain of the individual have undergone irreversible damage. Additionally, the indicators of hypodensity can indicate that there is at least a threshold probability of damage taking place with respect to the one or more second regions.

In one or more implementations, the first regions determined based on the first imaging data generated using the first imaging technique and the second regions determined based on the second imaging data generated using the second imaging technique can have at least a partial amount of overlap. In various examples, the one or more second regions can include portions of brain tissue that are not included in the one or more first regions. In these situations, a combination of the one or more first regions and the one or more second regions can provide a more accurate indication of brain tissue damage with respect to the individual than either the one or more first regions by themselves or the one or more second regions by themselves. In one or more illustrative examples, a user interface can be generated that includes an image derived from the first imaging data and that includes both a first overlay displaying the one or more first regions and a second overlay displaying the one or more second regions. In this way, a healthcare practitioner viewing the user interface via a computing device can be provided with a more accurate view of brain tissue damage with respect to the individual. Accordingly, the healthcare practitioner can indicate treatment options for the individual that can be safer and more effective than if the healthcare practitioner viewed the information provided by existing systems related to an amount of damage to brain tissue of the individual.

FIG. 1 is a diagrammatic representation of an architecture 100 for generating images that aggregate data from different imaging modalities and that include overlays indicating potential damage to brain tissue, according to one or more example implementations. In one or more examples, the architecture 100 can be implemented to generate user interfaces indicating brain tissue that has been irreversibly damaged. The architecture 100 can include an image processing system 102. The image processing system 102 can be implemented by one or more computing devices 104. The one or more computing devices 104 can include one or more server computing devices, one or more desktop computing devices, one or more laptop computing devices, one or more tablet computing devices, one or more mobile computing devices, or combinations thereof. In certain implementations, at least a portion of the one or more computing devices 104 can be implemented in a distributed computing environment. For example, at least a portion of the one or more computing devices 104 can be implemented in a cloud computing architecture.

The image processing system 102 can include a perfusion image processing system 106. The perfusion image processing system 106 can obtain first imaging data 108 that is generated by a first imaging technique 110. The first imaging technique 110 can be a perfusion-based imaging technique. In one or more examples, the first imaging technique 110 can be a computed tomography (CT) based imaging technique. In one or more illustrative examples, the first imaging technique 110 can be a CT-perfusion based imaging technique. In one or more additional illustrative examples, the first imaging technique 110 can be a CT-angiography based imaging technique.

The first imaging data 108 can correspond to one or more images of a brain 112 of an individual 114 captured by a CT imaging apparatus. In one or more examples, the CT imaging apparatus can capture a number of images of the brain 112 of the individual 114 over a period of time. In this way, a series of images of the brain 112 can be captured in succession over the period of time. Individual images in the series of images can be referred to herein as "slices." The slices can correspond to different regions of the brain 112. For example, a CT imaging apparatus can begin capturing slices of the shoulder or neck of the individual 114 and move up through the base of the skull through the brain 112 and to top of the head of the individual 114. In one or more examples, the CT imaging apparatus can capture multiple images of a same or similar region of the brain 112 of the individual 114 over time. As part of the imaging process, a contrast agent can be delivered to the individual 114, such as via an intravenous injection. The first imaging data 108 can include images of the brain 112 of the individual 114 that indicate the brain 112 before the contrast agent is delivered and images of the brain 112 of the individual 114 that indicate the presence of the contrast agent in one or more regions of the brain 112.

The first imaging data 108 can indicate intensity values of voxels of the images captured of the brain 112 of the individual 114. The intensity values can be indicated in Hounsfield units. In one or more examples, the intensity values of voxels that correspond to regions of the brain 112 in which the contrast agent is present can be greater than the intensity values of voxels that correspond to regions of the brain 112 in which the contrast agent is not present. In various examples, intensity values of voxels included in the first imaging data 108 can indicate an amount of contrast agent present in a region of the brain 112. To illustrate, as the amount of contrast agent present within a region of the brain 112 increases, the intensity values of voxels that correspond to the region can also increase. Further, as the amount of contrast agent present in a region of the brain 112 decreases, the intensity values of voxels that correspond to the region can also decrease.

In one or more examples, the first imaging data 108 can be formatted according to a Digital Imaging and Communications in Medicine (DICOM) standard. In addition to data that corresponds to images captured by a CT imaging apparatus, the first imaging data 108 can include additional information about the images captured by the CT imaging apparatus. For example, the first imaging data 108 can include timing data indicating a time at which individual slices of the brain 112 of the individual 114 are captured and/or a time interval at which the individual slices of the brain 112 of the individual 114 are captured. In addition, the first imaging data 108 can indicate characteristics of the slices. To illustrate, the first imaging data 108 can indicate at least one of slice thickness, inter-slice distance, voxel dimensions, or voxel locations. The first imaging data 108 can also indicate further information, such as at least one of information corresponding to the individual 114, information corresponding to a facility at which the first imaging data 108 was generated, or information corresponding to a CT imaging apparatus that captured the images of the brain 112 of the individual 114 included in the first imaging data 108.

The perfusion image processing system 106 can analyze the first imaging data 108 and generate one or more perfusion parameters 116. The one or more perfusion parameters 116 can indicate a flow of blood through one or more regions of the brain 112 of the individual 114. The one or more perfusion parameters 116 can include a measure of cerebral blood flow (CBF). In addition, the one or more perfusion parameters 116 can include a measure of cerebral blood volume (CBV). Further, the one or more perfusion parameters 116 can include a measure of mean tracer transit time (MTT). MTT can correspond to an average transit time of contrast agent through a region of the brain. The one or more perfusion parameters 116 can also include $T_{max}$ that corresponds to a peak of the tissue residue function. The tissue residue function indicates a probability that an amount of the contrast agent that entered a voxel remains inside the voxel at a later time. The one or more perfusion parameters 116 can be determined for individual voxels in at least a portion of the first imaging data 108.

In various examples, the perfusion image processing system 106 can analyze the intensity values of voxels of the first imaging data 108 with respect to one or more regions of the brain 112 to determine the one or more perfusion parameters 116. For example, the perfusion image processing system 106 can register one or more images included in the first imaging data 108 with a template image. The template image can comprise an anatomical template that is derived from images of brains of many individuals. After being registered with the template image, the one or more images included in the first imaging data 108 can be aligned with an atlas that indicates a number of regions of a human brain. In various examples, the atlas can indicate locations of blood vessels, parenchyma, and so forth. In this way, the number of regions can be identified with respect to the one or more images included in the first imaging data 108. In one or more examples, the one or more images of the first imaging data 108 can be labeled according to the number of regions included in the atlas. The perfusion image processing system 106 can then analyze the intensity values of voxels that correspond to one or more of the regions over a period of time to determine the one or more perfusion parameters 116. To illustrate, the perfusion image processing system 106 can analyze intensities of voxels that correspond to blood vessels of the brain 112 to determine the one or more perfusion parameters 116.

The perfusion image processing system 106 can also analyze the one or more perfusion parameters 116 in conjunction with the first imaging data 108 to determine one or more regions of the brain 112 that have been damaged tissue due to a disrupted supply of blood to the one or more regions. For example, the first imaging data 108 can include a first image 118 of the brain 112 of the individual 114. In one or more illustrative examples, the first image 118 can include a slice captured by a CT imaging apparatus at a given time. The first image 118 can indicate blood vessels 120 in which a contrast agent is present. The perfusion image processing system 106 can analyze the one or more perfusion parameters 116 and intensity values of voxels corresponding to the blood vessels 120 that supply blood to a section 122 of the brain 112 to determine an extent of the disruption of the flow of blood to the section 122 and an amount of time of disruption to the flow of blood to the section 122. Based on the extent of the disruption of blood flow to the section 122, the perfusion image processing system 106 can determine a first region of interest 124 of the section 122 that has at least a threshold probability of having damaged tissue. In one or more implementations, the perfusion image processing system 106 can generate first overlay imaging data 126 that corresponds to a first overlay that indicates the first region of interest 124. In one or more examples, the first overlay can be displayed in conjunction with the first image 118.

The perfusion image processing system 106 can determine a region having damaged brain tissue based on individual perfusion parameters 116. For example, the perfusion image processing system 106 can determine a region having at least at threshold probability of including damaged brain tissue based on one or more measures of cerebral flood flow for voxels included in the region. In one or more additional examples, the perfusion image processing system 106 can determine a region having damaged brain tissue based on one or more values for $T_{max}$. In one or more further examples, the perfusion image processing system 106 can determine a region having damaged brain tissue based on one or more values for cerebral blood volume. The perfusion image processing system 106 can determine a region having damaged brain tissue based on one or more values of mean tracer transit time. In still additional examples, the perfusion image processing system 106 can determine a region having damaged brain tissue based on one or more values of at least one of cerebral blood flow, cerebral blood volume, $T_{max}$, or mean tracer transit time.

In one or more illustrative examples, the perfusion image processing system 106 can determine an amount of damaged brain tissue and/or a predicted amount of damaged brain tissue based on differences between regions identified using two or more of the perfusion parameters 116. To illustrate, the perfusion image processing system 106 can determine a first region having at least a threshold probability of including damaged brain tissue using a value of cerebral blood flow and a second region having at least a threshold probability of including damaged brain tissue using a value of $T_{max}$. In one or more examples, the first region can correspond to an approximation of the amount of damaged brain tissue at a first time and the second region can correspond to an approximation of the amount of damaged brain tissue at a later, second time, where the second region is greater in volume than the first region. In these scenarios, the difference between the volumes of the first region and second region can indicate that over time the first region can increase in volume to the volume of the second region. In various examples, an intervention prescribed to treat or minimize the amount of damaged brain tissue can be based on the difference between the volumes of the first region and the second region. For example, a first treatment can be prescribed in situations where the difference between volumes of the first region and the second region are less than a threshold difference and a second treatment can be prescribed in instances where the difference between the volumes of the first region and the second region is greater than or equal to the threshold difference.

The perfusion image processing system 106 can also implement one or more machine learning techniques to determine regions of tissue in the brain 112 of the individual 114 that has been damaged. In various examples, the one or more machine learning techniques can be used to determine regions of tissue in the brain 112 of the individual 114 that have at least a threshold probability of being damaged. In one or more examples, one or more convolutional neural networks may be implemented to determine regions of potentially damaged tissue in the brain 112 of the individual 114. For example, a U-Net architecture may be implemented to determine regions of damaged tissue in the brain 112 of the individual 114. Additionally, one or more classification convolutional neural networks can be implemented to determine regions of damaged tissue in the brain 112 of the individual 114. In one or more illustrative examples, the hypodensity analysis system 128 can obtain a number of CT-perfusion images as training images. The training images can include a first number of images of the brains of first individuals having one or more damaged regions and a second number of images of brains of second individuals that do not include damaged regions. In one or more scenarios, the first number of images can be classified as having one or more damaged regions and the second number of images can be classified as not having a damaged region. In one or more further examples, specified regions of the brains of the first individuals included in the first images can be classified as damaged regions. Values of parameters of one or more models generated in conjunction with the one or more machine learning techniques can be determined through a training process. After the training process is complete and the one or more models have been validated using an additional set of images, regions of new images that have been damaged can be classified using the one or more models.

The image processing system 102 can also include a hypodensity analysis system 128. The hypodensity analysis system 128 can determine density values of one or more regions of the brain 112 of the individual 114 based on second imaging data 130. In one or more examples, the hypodensity analysis system 128 can determine one or more regions of the brain 112 of the individual 114 that includes tissue having density values that are less than one or more threshold values. In various examples, brain tissue having density values less than the one or more threshold values can indicate that damage has occurred with respect to the brain tissue.

The second imaging data 130 can be generated by a second imaging technique 132. The second imaging technique 132 can be a non-perfusion-based imaging technique. In various examples, the second imaging technique 132 can be a non-contrast agent-based imaging technique. In one or more illustrative examples, the second imaging technique 132 can implement one or more non-contrast CT imaging techniques. The second imaging technique 132 can however also be replaced by one or more images from the first imaging technique 110, specifically images that are acquired before the imaging contrast agent reaches the brain. In these scenarios, the first imaging technique 110 and the second imaging technique 132 may include a same imaging modality with the first imaging data 108 and the second imaging data 130 being captured at different times. To illustrate, the first imaging data 108 can be captured by an imaging technique, such as CT-perfusion, during a period of time when a contrast agent is present in the brain 112 of the individual 114 and the second imaging data 130 can be captured by the same imaging modality, during a period of time when a contrast agent is absent from the brain 112 of the individual 114.

The second imaging data 130 can correspond to one or more images of the brain 112 of the individual 114 captured by a CT imaging apparatus. In one or more examples, the CT imaging apparatus can capture a number of images of the brain 112 of the individual 114 over a period of time. In this way, a series of images of the brain 112 can be captured in succession over the period of time. The slices can correspond to different regions of the brain 112. For example, a CT imaging apparatus can begin capturing images of the shoulder or neck of the individual 114 and move up through the base of the skull through the brain 112 and to top of the head of the individual 114. In one or more examples, the CT imaging apparatus can capture multiple images of a same or similar region of the brain 112 of the individual 114 over time.

The second imaging data 130 can indicate intensity values of voxels of the images captured of the brain 112 of the individual 114. The intensity values can be indicated in Hounsfield units. In one or more examples, the intensity values of voxels that correspond to regions of the brain 112 having a relatively lower density have relatively lower intensity values in relation to regions of the brain 112 having relatively higher density. In these scenarios, the intensity values of voxels included in the second imaging data 130 increases as the brain tissue corresponding to the voxels increases in density.

In one or more examples, the second imaging data 130 can be formatted according to a Digital Imaging and Communications in Medicine (DICOM) standard. In addition to data that corresponds to images captured by a CT imaging apparatus, the second imaging data 130 can include additional information about the images captured by the CT imaging apparatus. For example, the second imaging data 130 can include timing data indicating a time at which individual slices of the brain 112 of the individual 114 are captured and/or a time interval at which the individual slices of the brain 112 of the individual 114 are captured. In addition, the second imaging data 130 can indicate characteristics of the slices. To illustrate, the second imaging data 130 can indicate at least one of slice thickness, inter-slice distance, voxel dimensions, or voxel locations. The second imaging data 130 can also indicate further information, such as at least one of information corresponding to the individual 114, information corresponding to a facility at which the first imaging data 108 was generated, or information corresponding to a CT imaging apparatus that captured the images of the brain 112 of the individual 114 included in the second imaging data 130.

In various examples, the hypodensity analysis system 128 can analyze the intensity values of voxels of the second imaging data 130 with respect to one or more regions of the brain 112 to determine Hounsfield density values of regions of the brain 112 and identify regions of the brain 112 that have been damaged tissue based on the Hounsfield density values. In various examples, the hypodensity analysis system 128 can analyze intensity values of voxels included in the second imaging data 130 to determine regions of the brain 112 of the individual 114 that have at least a threshold probability of being damaged. In one or more examples, the hypodensity analysis system 128 can register one or more images included in the second imaging data 130 with a template image. The template image can comprise an anatomical template that is derived from images of brains of many individuals. After being registered with the template image, the one or more images included in the second imaging data 130 can be aligned with an atlas that indicates a number of regions of a human brain. In this way, the number of regions can be identified with respect to the one or more images included in the second imaging data 130. In one or more examples, the one or more images of the second imaging data 130 can be labeled according to the number of regions included in the atlas. To illustrate, the hypodensity analysis system 128 can use the atlas to determine ventricles of the brain 112, cerebrospinal fluid in the brain 112, and soft tissue of the brain 112, such as parenchyma and additional blood vessels.

In one or more examples, the hypodensity analysis system 128 can analyze voxels in different hemispheres of the brain 112 to determine one or more regions of the brain 112 that include hypodense tissue. In one or more illustrative examples, the second imaging data 130 can include a second image 134 of the brain 112 of the individual 114. In various examples, the second image 134 can include a slice captured by a CT imaging apparatus at a given time using one or more non-contrast CT imaging techniques. The hypodensity analysis system 128 can determine a spatial correlation between voxels included in a first hemisphere 136 of the brain 112 and a second hemisphere 138 of the brain 112. In one or more examples, the first hemisphere 136 and the second hemisphere 138 can be referred to herein as being contralateral with respect to one another. In addition, a first voxel located in the first hemisphere 136 that spatially corresponds to a second voxel located in the second hemisphere 138 can be referred to herein as being contralateral with respect to one another.

The hypodensity analysis system 128 can then analyze intensity values of voxels located in the first hemisphere 136 with respect to intensity values of voxels located in the second hemisphere 138. In various examples, the hypodensity analysis system 128 can determine differences between contralateral voxels location in the first hemisphere 136 and the second hemisphere 138. In one or more examples, the hypodensity analysis system 128 can determine one or more regions of the brain 112 having first voxels with at least a threshold difference in intensity values in relation to contralateral second voxels. In the illustrative example of FIG. 1, the hypodensity analysis system 128 can determine that a second region of interest 140 of the second hemisphere 138 includes voxels having at least a threshold difference in intensity values with respect to voxels location in the first hemisphere 136 that are contralateral with respect to the voxels location in the second region of interest 140. In one or more examples, the second region of interest 140 can indicate brain tissue that has been damaged due to disruption to the supply of blood to the second region of interest 140. In one or more additional examples, the hypodensity analysis system 128 can determine the second region of interest 140 using one or more machine learning techniques rather than or in addition to the contralateral analysis of intensity values of voxels location in the first hemisphere 136 and the second hemisphere 138. In one or more implementations, the hypodensity analysis system 128 can generate second overlay imaging data 142 that corresponds to a second overlay that indicates the second region of interest 140. In one or more examples, the first overlay can be displayed in conjunction with the second image 134.

The hypodensity analysis system 128 can also implement one or more machine learning techniques to determine regions of hypodense tissue in the brain 112 of the individual 114. In one or more examples, one or more convolutional neural networks may be implemented to determine regions of hypodense tissue in the brain 112 of the individual 114. For example, a U-Net architecture may be implemented to determine regions of hypodense tissue in the brain 112 of the individual 114. Additionally, one or more classification convolutional neural networks can be implemented to determine regions of hypodense tissue in the brain 112 of the individual 114. In one or more illustrative examples, the hypodensity analysis system 128 can obtain a number of non-contrast CT images as training images. The training images can include a first number of images of the brains of first individuals having one or more hypodense regions and a second number of images of brains of second individuals that do not include hypodense regions. In one or more scenarios, the first number of images can be classified as having one or more hypodense regions and the second number of images can be classified as not having a hypodense region. In one or more further examples, specified regions of the brains of the first individuals included in the first images can be classified as hypodense regions. Values of parameters of one or more models generated in conjunction with the one or more machine learning techniques can be determined through a training process. After the training process is complete and the one or more models have been validated using an additional set of images, hypodense regions of new images can be classified using the one or more models.

The image processing system 106 can include an output image system 144. The output image system 144 can obtain the first overlay imaging data 126 and the second overlay imaging data 142 to generate one or more aggregate images 146. The one or more aggregate images 146 can include a first overlay that corresponds to the first overlay imaging data 126 and a second overlay that corresponds to the second overlay imaging data 142. In one or more examples, the output image system 144 can generate the one or more aggregate images 146 using at least one of the first imaging data 108 or the second imaging data 130 in conjunction with the first overlay imaging data 126 and the second overlay imaging data 142. For example, the output image system 144 can generate the one or more aggregate images 146 to include an image of the first imaging data 108 with a first overlay corresponding to the first overlay imaging data 126 and a second overlay corresponding to the second overlay imaging data 142. In one or more illustrative examples, the output image system 144 can generate the one or more aggregate images 146 to include the first image 118 having a first overlay that corresponds to the first region of interest 124 and a second overlay that correspond to the second region of interest 140.

In one or more examples, taken individually the first region of interest 124 may indicate an amount of damaged brain tissue that is less than an actual amount of damaged brain tissue. In these scenarios, the first region of interest 124 can have a volume that is less than a volume of the second region of interest 140. Thus, by generating the one or more aggregate images 146 showing the difference in volume between the first region of interest 124 and the second region of interest 140, the output image system 144 can provide a user interface including the aggregate images 146 to healthcare practitioners indicating a more accurate estimate of damage to tissue of the brain 112. As a result, patient selection for reperfusion therapy can be improved and potentially futile treatments, such as where the entire hypoperfused regions have already become infarcted, can be avoided.

Although not shown in the illustrative example of FIG. 1, the image processing system 102 can also include a brain tissue damage and at-risk analysis system. The brain tissue damage and at-risk analysis system can determine differences in volumes of regions of interest of determined using different perfusion parameters 116. For example, the brain tissue damage and at-risk analysis system can determine a first volume of a first region of interest according to a first perfusion parameter at a first threshold, for example the infarct region, and a second volume of a second region of interest according to a second perfusion parameter at a second threshold, for example the at-risk region plus infarct region. To illustrate, the brain tissue damage and at-risk analysis system can determine a first volume of a first region of the brain 112 based on relative cerebral blood flow in the first region being at least 30% less than the relative cerebral blood flow in a contralateral region of the brain 112. Additionally, the brain tissue damage and at-risk analysis system can determine a second volume of a second region of the brain 112 having a $T_{max}$ that is greater than 6 seconds. A difference between the first volume and the second volume can be calculated, i.e. the tissue at risk, and displayed within a user interface. In one or more illustrative examples, the difference between the first volume and the second volume can be referred to herein as a mismatch volume. Additionally, a ratio between the first volume and the second volume can also be calculated and displayed within a user interface. The ratio between the first volume and the second volume can be referred to herein as a mismatch ratio. In various examples, the mismatch volume and the mismatch ratio can be used by healthcare practitioners to determine recommendations for treatment of individuals having at least a threshold probability of brain tissue damage.

Further, although not shown in the illustrative example of FIG. 1, the first imaging technique 110 can include a CT-angiography imaging system and the first imaging data 108 can include CT-angiography images. In these scenarios, the image processing system 102 may include an additional image processing system to determine one or more regions of the brain 112 having damaged tissue based on the CT-angiography images. In one or more examples, the additional image processing system can derive a core region of the brain 112 by identifying regions of one or more CT-angiography images in which subtle signal enhancement is absent and also determining narrowing of vessels of the brain 112 based on the one or more CT-angiography images. regions of the brain 112. The narrowing of vessels in one or more regions of the brain 112 can be analyzed to determine a probability of the one or more regions having damaged tissue or to determine a measure of damage to the one or more regions. In various examples, one or more machine learning techniques can be implemented to analyze the narrowing of vessels of the brain to determine regions of the brain 112 of the individual 114 including damaged tissue. To illustrate, a number CT-angiography training images can be obtained. The training images can include a first number of images of the brains of first individuals having narrowing of vessels in damaged regions of the brain and a second number of images of brains of second individuals that do not include narrowing of vessels that resulted in damaged tissue. The first number of images can be classified as having at least one region with damaged tissue and the second number of images can be classified as not having a damaged region. In one or more additional examples, specified regions of the brains of the first individuals included in the first images can be classified as damaged regions. Values of parameters of one or more models generated in conjunction with the one or more machine learning techniques can be determined through a training process. After the training process is complete and the one or more models have been validated using an additional set of images, regions of brains included in new images can be classified using the one or more models as including damaged tissue or not including damaged tissue.

Figure 2:
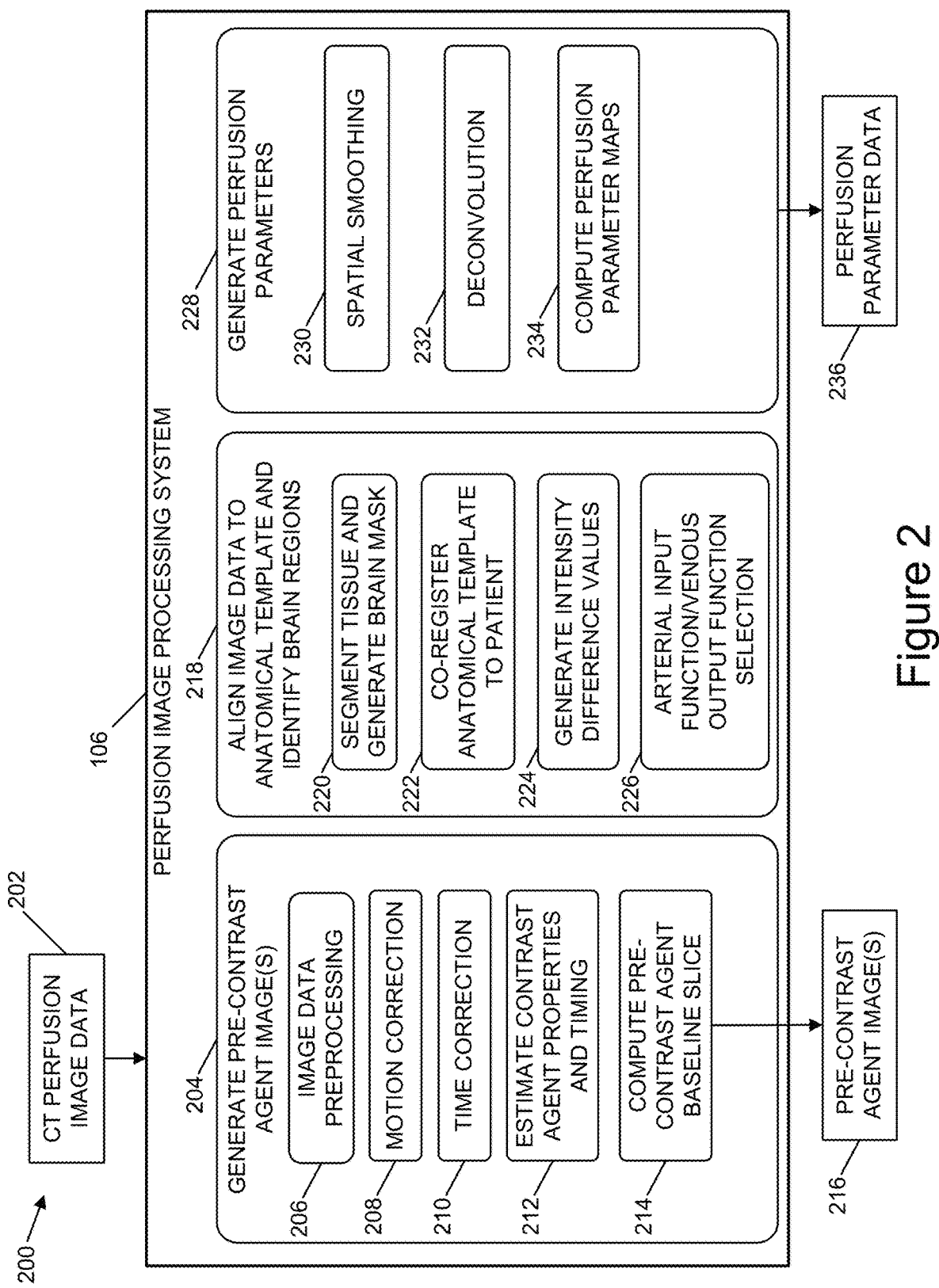
FIG. 2 is a diagrammatic representation of an example architecture to determine perfusion parameters with respect to the flow of blood through the brain of an individual, according to one or more example implementations.

FIG. 2 is a diagrammatic representation of an architecture 200 to determine perfusion parameters with respect to the flow of blood through the brain of an individual, according to one or more example implementations. The architecture 200 can include the perfusion image processing system 106. The perfusion image processing system 106 can obtain CT perfusion image data 202. The CT perfusion image data 202 can be captured by a CT imaging apparatus. During a perfusion-based CT imaging process, a contrast agent can be delivered to an individual and the presence and movement of the contrast agent through the brain of the individual can be captured during the perfusion-based imaging process. The presence and movement of the contrast agent through the brain of the individual can correspond to the presence and movement of blood through the brain of the individual. In addition, the CT perfusion image data 202 can include a number of images captured over a period of time. The number of images included in the CT perfusion image data 202 can be referred to herein as slices. The CT perfusion image data 202 can be formatted and include information corresponding to the DICOM standard.

The perfusion image processing system 106 can perform a number of processes, such as generating one or more pre-contrast agent images at operation 204. To illustrate, the perfusion image processing system 106 can, at operation 206, perform a number of operations to analyze the CT perfusion image data 202 at operation 206 with respect to a number of rules in order for the CT perfusion image data 202 to be processed by the perfusion image processing system 106. For example, the perfusion image processing system 106 can analyze, at operation 206, the CT perfusion image data 202 to determine whether the CT perfusion image data 202, such as tags, related to the timing of the capture of images are included in the CT perfusion image data 202. The timing of sampling of images included in the CT perfusion image data 202 can be determined at operation 206 based on timing tags included in the CT perfusion image data 202. In one or more examples, the perfusion image processing system 106 can determine an amount of the CT perfusion image data 202 to be processed based on a maximum time threshold for a scan used to capture the CT perfusion image data 202, such as 1000 seconds. The perfusion image processing system 106 can also, at operation 206, determine whether the CT perfusion image data 202 includes tags indicating image positioning, spacing, and orientation. The information included in the CT perfusion image data 202 can be used by the perfusion image processing system 106 to determine the processing of overlapping slices. The operation 206 can also determine whether the CT perfusion image data 202 includes information that the perfusion image processing system 106 can use to compute regions of interest that can indicate brain tissue that is damaged and is at risk of infarct.

At operation 208, the perfusion image processing system 106 can perform a motion correction process. In various examples, patient motion during image acquisition can degrade the quality of perfusion images. The motion correction process at operation 208 can reduce the effect of patient movement during image acquisition. The motion correction process at operation 208 can include 3-dimensional (3D) rigid body co-registration for spatial misalignment. In one or more examples, time points in the perfusion series are aligned with a reference volume. The reference volume can be a volume that is most similar to as many other volumes of the CT perfusion image data 202. To illustrate, individual slices included in the CT perfusion image data 202 can be analyzed to determine similarity metrics with respect to each other. The similarity measure of individual slices can be optimized to determine a slice that has a greatest value of a similarity metric with respect to a greatest number of additional image slices. In one or more implementations, at least a portion of the slices that are not determined to be the reference image can be analyzed with respect to the reference image and can be identified as slices that correspond to movement of the individual during the imaging process. In one or more illustrative examples, the similarity measures can be determined using a mean squared difference procedure.

For individual image slices, rotational parameters and/or translational parameters can be determined that optimize the similarity between the individual image slices and the reference image. The translational parameters and/or rotational parameters can be used to realign the image segment. In one or more illustrative examples, a slice can be resampled with respect to the reference image to modify at least one of the position or size of voxels of the slice to correspond to the position and/or size of voxels of the reference image. To illustrate, a slice capturing an image during a period of time that the individual is moving can be resampled with the rotation and translation parameters into a new position in situations where the difference in position with respect to the reference image is more than a specified amount, such as 10% of a voxel in any dimension, 25% of a voxel in any dimension, half a voxel in any dimension, or 75% of a voxel in any dimension. The dimensions of a voxel can be identified by perfusion image processing system 106 from information included in the CT perfusion image data 202. In this way, a slice is resampled in situations where a cost function is optimized and the change in position leads to at least a threshold amount of improved alignment between the reference image and a number of the additional slices.

In various examples, the motion correction process at operation 206 can be used to determine corrupted slices that have less than a threshold amount of alignment with the reference image. The corrupted slices can be labeled by the perfusion image processing system 106 and may not utilized in the computation of perfusion parameters by the perfusion image processing system 106. An end result of the motion correction process at operation 208 can be to generate motion corrected image data that maximizes a number of slices included in the CT perfusion image data 202 that are aligned such that anatomic structures included in slices of the CT perfusion image data 202 are in a relatively same or similar position as the anatomical structures of the reference image. In one or more examples, non-anatomical structures, such as a head holder that holds the head of the individual during the imaging process can be removed.

At operation 210, a time correction process can be performed by the perfusion image processing system 106 based on slices of the CT perfusion image data 202 being acquired at varying time intervals. The time correction process performed at operation 210 can be performed with respect to the motion corrected data generated by the motion correction process performed at operation 208. Time correction operations can include resampling the CT perfusion image data 202 onto a common time axis having regularly spaced time intervals. The regularly spaced time intervals can be from about 0.1 seconds to about 2 seconds, from about 0.1 seconds to 1 second, from about 0.5 seconds to 2 seconds, from about 1 second to 2 seconds, or from about 0.5 seconds to about 1 second. In one or more illustrative examples, the regularly spaced time intervals can be 1 second. In one or more additional illustrative examples, the regularly spaced time intervals can be 0.5 seconds. In one or more further illustrative examples, the regularly spaced time intervals can be 2 seconds. In still other illustrative examples, the regularly spaced time intervals can be 0.25 seconds. The time correction process performed at operation 210 can include determining a piecewise linear curve for each spatial position represented by coordinates on the X-, Y-, and Z-axis using the portions of the CT perfusion image data 202 relating the voxels of the slices and based on the timing data included in the CT perfusion image data 202. The piecewise linear curves for each spatial position can be resampled into defined, regular time intervals to generate a temporally resolved dataset having a common time interval. Timing data for corrupted slices determined from the motion correction process performed at operation 208 and that have been removed from the motion corrected data can be interpolated using linear interpolation based on the slices captured at neighboring time points with respect to the corrupted slices.

The perfusion image processing system 106 can also perform a process at operation 212 to estimate contrast agent properties and timing with respect to the CT perfusion image data 202. For example, at operation 212, the perfusion image processing system 106 can determine the arrival time of the contrast agent with respect to voxels that correspond to brain tissue. The brain tissue can include blood vessels and blood located within the blood vessels. In various examples a mean contrast agent transport curve can be generated by determining the average of the signal change across voxels that correspond to brain tissue at a given point in time. A contrast agent arrival time for one or more voxels can be determined using information determined from the mean contrast agent transport curve. The contrast agent arrival time can be used to determine a baseline time frame that includes a time from the beginning of the CT scan to the contrast agent arrival time. The baseline time frame can be subsequently used by the perfusion image processing system 106 to determine perfusion parameters for the CT perfusion image data 202. For example, at operation 214, the pre-contrast agent baseline images 216 of the CT perfusion image data 202 can be determined as an average of the slices that are within the baseline time range before the contrast agent arrives. The pre-contrast agent baseline images 216 can be provided for subsequent processing by the perfusion image processing system 106. For example, the pre-contrast agent baseline images 216 can be used at operation 218 to align image data to an anatomical template and to identify regions of the brain of the individual. The pre-contrast agent baseline images 216 can also be provided to the output image system 144 to use when generating an aggregate image with overlays. In various examples, the pre-contrast agent baseline images 216 can be used to perform a registration of non-perfusion-based images into the perfusion-based imaging space.

The alignment of the CT perfusion image data 202 to an anatomical template and the identification of brain regions of the individual based on the CT perfusion image data 202 can include segmenting brain tissue and generating a brain mask at operation 220. The brain mask can be determined based on the pre-contrast agent baseline images 216 computed before the arrival of the contrast agent. The brain mask can include a two-dimensional image of features of a brain of an individual, such as brain tissue that includes blood vessels and parenchyma. Additional features included in the pre-contrast agent baseline images 216 can be removed, such as the scalp, dura matter, fat, skin, muscles, eyes, and bones. The brain mask can be generated by performing morphological operations, such as opening and closing, with respect to voxels of the pre-contrast agent baseline images 216. The morphological operations can be followed by connected-component analysis techniques to remove the non-brain features from the pre-contrast agent baseline images 216 to generate the brain mask. One or more intensity value thresholds can be used to determine voxels to be used to generate the brain mask. In one or more examples, at least one of relative or absolute intensity value thresholds can be used.

In implementations where the CT perfusion image data 202 is generated using CT imaging techniques having anatomical coverage along the Z-axis of less than a threshold amount, such as 5 mm, 10 mm, 20 mm, 30 mm, 40 mm, 50 mm, 60 mm, or 75 mm, a segmentation process can be performed at operation 220 to generate a brain mask. The anatomical coverage of a CT imaging technique can correspond to at least one of a number of data channels, number of detector rows, pitch, section thickness, scanning time, or gantry rotation time. The segmentation process can determine a segmentation threshold that includes a range of intensity values. The range of intensity values can correspond to brain tissue based on previously determined intensity values for brain tissue. A voxel may be included in the brain mask based on determining that the intensity value of the voxel is included in the range of values that corresponds to the segmentation threshold. Additionally, a voxel may be excluded from the brain mask based on determining that the intensity value of the voxel is outside of the range of values that corresponds to the segmentation threshold.

In situations where the CT perfusion image data 202 is generated using CT imaging techniques having anatomical coverage along the Z-axis of at least the threshold amount, the brain mask can be determined at operation 222 using an anatomical template that is co-registered to the CT perfusion image data 202 to identify intracranial tissue. The anatomical template can include a composite image of a human skull and brain that is generated from a number of CT images of human brains. The CT perfusion image data 202 can be elastically co-registered with the anatomical template to produce modified image data. The modified image data can correspond to parameters indicating an amount of modification of the CT perfusion image data 202 to correspond to the anatomical template. In various examples, a deformation field can be generated based on the registration process. In one or more examples, the deformation field can be applied to an atlas that indicates a number of regions of the brains of individuals. The atlas can be generated based on respective locations of individual regions of the brain derived from a number of images of the brains of a number of individuals. The atlas can be transformed to correspond to the CT perfusion image data 202 and the brain mask for the CT perfusion image data 202 can be generated based on the regions of the CT perfusion image data 202 that correspond to the modified atlas. In one or more implementations, a brain mask determined using the procedure performed with respect to operation 220 in situations where the anatomical coverage along the Z-axis is at least the threshold amount can be combined with a brain mask determined using the procedure performed in situations where the anatomical coverage along the Z-axis is no greater than the threshold amount at operation 222.

An operation 224 can include generating intensity difference values of voxels corresponding to an effect of the contrast agent effect being present in voxels of the CT perfusion image data 202. The CT perfusion image data 202 can be modified to indicate the contrast agent effect by removing the information included in the CT perfusion image data 202 that corresponds to a period of time that the contrast agent was not present in a location of one or more voxels. In various examples, operations used to determine the intensity values of voxels that correspond to the presence of a contrast agent can be based on one or more imaging techniques that generate the image data. For example, in situations where computed tomography is used to generate the CT perfusion image data 202, intensity values of pixels that correspond to the presence of contrast agent can be determined based on values of a contrast agent concentration curve that indicates intensity values in Hounsfield units (HU) of voxels at a number of locations at a given time. In one or more examples, the values for the concentration curve can be based on a difference between an intensity value in the CT-perfusion image data at a given location at a specified time and a baseline intensity value. In one or more illustrative examples, the baseline value can be determined based on the averaged pre-contrast agent baseline slice determined at operation 214.

The process of aligning the image data to an anatomical template and identifying regions of the brain of the individual at operation 218 can also include determining an arterial input function (AIF) and a venous output function (VOF) at operation 226. Operation 226 can include determining an arterial input function by determining a cluster of voxels that correspond to a large vessel located within the brain. The arterial input function can indicate the concentration of contrast agent over time for a relatively large input artery. In one or more examples, the arterial input function can be based on vessels located in the middle cerebral artery of the brain or the anterior cerebral artery. In additional examples, such as where the anatomical coverage is less than a threshold value for computed tomography imaging, candidate clusters of voxels for the arterial input function can be determined in portions of the CT perfusion image data 202 that correspond to anterior and posterior portions of the brain after bone and other non-brain tissue have been removed.

The venous output function can be determined by determining a cluster of voxels that correspond to a large vessel located within the brain. The venous input function can indicate the concentration of contrast agent over time for a relatively large output vein. In one or more examples, the venous output function can be based on vessels located in the sagittal- and straight sinus vein areas of the brain. In additional examples, such as where the anatomical coverage is less than a threshold value for computed tomography imaging, candidate clusters can be determined in portions of the image data that correspond to anterior and posterior portions of the brain after bone and other non-brain tissue have been removed.

In one or more examples, the process at operation 226 for determining the arterial input function and the venous output function can include determining an amplitude of the contrast agent concentration curve, time of peak of the contrast agent concentration curve, and width of peak of the contrast agent concentration curve in each voxel that represents brain tissue with respect to the candidate voxels. In various examples, the highest peak for a given voxel can be used to determine the amplitude of the contrast agent concentration curve, peak time of the contrast agent concentration curve, and width of the peak of the contrast agent concentration curve for the given voxel. The peak information for individual voxels can be analyzed with respect to target peak shapes that correspond to a range of amplitude values, a range of time values, and a range of width values. A subset of the candidate voxels can be identified based on the analysis of peak information of the voxels according to one or more criteria. The one or more criteria can include a negative amplitude, a peak width that is less than a threshold peak width, or a peak that is outside of the rest of the at least a threshold number of peaks for voxels included in the CT perfusion image data 202. For the subset of voxels that satisfy the one or more criteria, the perfusion image processing system 106 can determine average values for peak amplitude, offset, and width. The perfusion image processing system 106 can also determine standard deviations for the peak amplitude, offset, and width values for the subset of candidate voxels. Values of peak information for respective voxels included in the subset of candidate voxels can be normalized in related to the average values for peak amplitude, offset, and width.

A score can be determined for the arterial input function for individual voxels included in the subset of candidate voxels. The score can be determined for an individual candidate voxel based on an amount that the amplitude value of the individual voxel is greater than an average amplitude value. The score can also be determined for an individual candidate voxel based on an amount that the offset value of the individual voxel is earlier than the average offset value. Additionally, the score can be determined for an individual candidate voxel based on an amount that the width of the peak is narrower than the average peak value.

The perfusion image processing system 106 can determine at least a threshold number of voxels having a greatest score. The threshold number of voxels can be from 10 to 50, from 12 to 45, from 15 to 30, or from 18 to 25. The perfusion image processing system 106 can also determine from this additional subset voxels that do not include a neighboring voxel included in the second group. The average arterial input function can be determined using the time versus contrast agent concentration curves for the remaining voxels.

A score can also be determined for the venous output function for individual voxels included in the subset of candidate voxels. The score can be determined for an individual candidate voxel based on an amount that the amplitude value of the individual voxel is greater than an average amplitude value. The score can be determined for candidate voxels having a contrast agent arrival time that is at least 0.5 seconds, at least 1 second, at least 2 seconds, at least 3 seconds, or at least 4 seconds after the arrival time for the contrast agent with respect to arterial input function. In one or more examples, the score can be determined for candidate voxels having a contrast agent arrival time from about 2 seconds to about 15 seconds after the arrival time for the contrast agent with respect to the arterial input function, from about 3 seconds to about 12 seconds after the arrival time for the contrast agent with respect to the arterial input function, from about 4 seconds to 10 seconds after the arrival time for the contrast agent with respect to the arterial output function, or from about 2 seconds to about 10 seconds after the arrival time for the contrast agent with respect to the arterial output function. The perfusion image processing system 106 can determine at least a threshold number of voxels having a greatest score. The threshold number of voxels can be from 10 to 50, from 12 to 45, from 15 to 30, or from 18 to 25. The perfusion image processing system 106 can also determine from this additional subset voxels that do not include a neighboring voxel included in the second group. The average venous output function can be determined using the time versus contrast agent concentration curves for the remaining voxels.

The perfusion image processing system 106 can also generate perfusion parameters at operation 228. Generating perfusion parameters can include, at operation 230, one or more spatial filtering operations to decrease noise included in at least a portion of the CT perfusion image data 202. For example, abrupt intensity changes can be removed by the one or more spatial filtering operations. To illustrate, a Gaussian smoothing kernel having a specified filter width that includes a minimum amount of spatial filtering to be applied up to a maximum amount of spatial filtering to be applied. In one or more illustrative examples, the minimum amount of spatial filtering can be 0.0 mm, 0.1 mm, 0.25 mm, 0.5 mm, 0.75 mm, or 1 mm. In one or more additional illustrative examples, the maximum amount of spatial filtering can be 7 mm, 8 mm, 9 mm, 10 mm, 11 mm, 12 mm or 13 mm. In various examples, data corresponding to the voxels that are used to calculate the arterial input function and the venous output function is excluded from the one or more spatial filtering operations. Additionally, in one or more implementations, voxels included in the CT perfusion image data 202 that are do not correspond to tissue of the brain can be excluded from the one or more spatial filtering operations.

Additionally, at operation 232, one or more deconvolution operations can be performed to determine a tissue residue function. The tissue residue function can describe a probability that an amount of contrast agent that entered a voxel at a given time remains in the voxel at a later time. The one or more deconvolution operations can be performed with respect to the contrast agent concentration versus time curves for voxels that correspond to brain tissue. In one or more examples, the one or more deconvolution operations can include implementing one or more Fourier Transforms that are normalized using one or more filters applied to the Fourier Transform spectra.

One or more perfusion parameters can be determined, at operation 234, for individual voxels included in individual slices of at least a portion of the CT perfusion image data 202. The one or more perfusion parameters can be included in perfusion parameter data 236. The perfusion parameter data 236 can be used by the perfusion image processing system 106 to determine brain tissue that has at least a threshold probability of being damaged and/or to determine brain tissue that is at risk of being damaged. In one or more situations, damaged brain tissue can be infarcted. Additionally, in various examples, the damaged brain tissue can be irreversibly damaged.

The one or more perfusion parameters can include relative cerebral blood volume (rCBV). The relative cerebral blood volume can be determined by determining the area under the tissue residue function. In addition, the one or more perfusion parameters can include relative cerebral blood flow (rCBF). The relative cerebral flood flow can be determined by determining a peak of the tissue residue function. Further, the one or more perfusion parameters can include mean tracer transit time (MTT). The mean tracer transit time for individual voxels can be determined using the central volume principle. The central volume principle indicates that MTT=CBV/CBF. In one or more additional examples, the one or more perfusion parameters can include $T_{max}$. $T_{max}$ can be determined can be identified by determining a peak of the tissue residue function.

Figure 3:
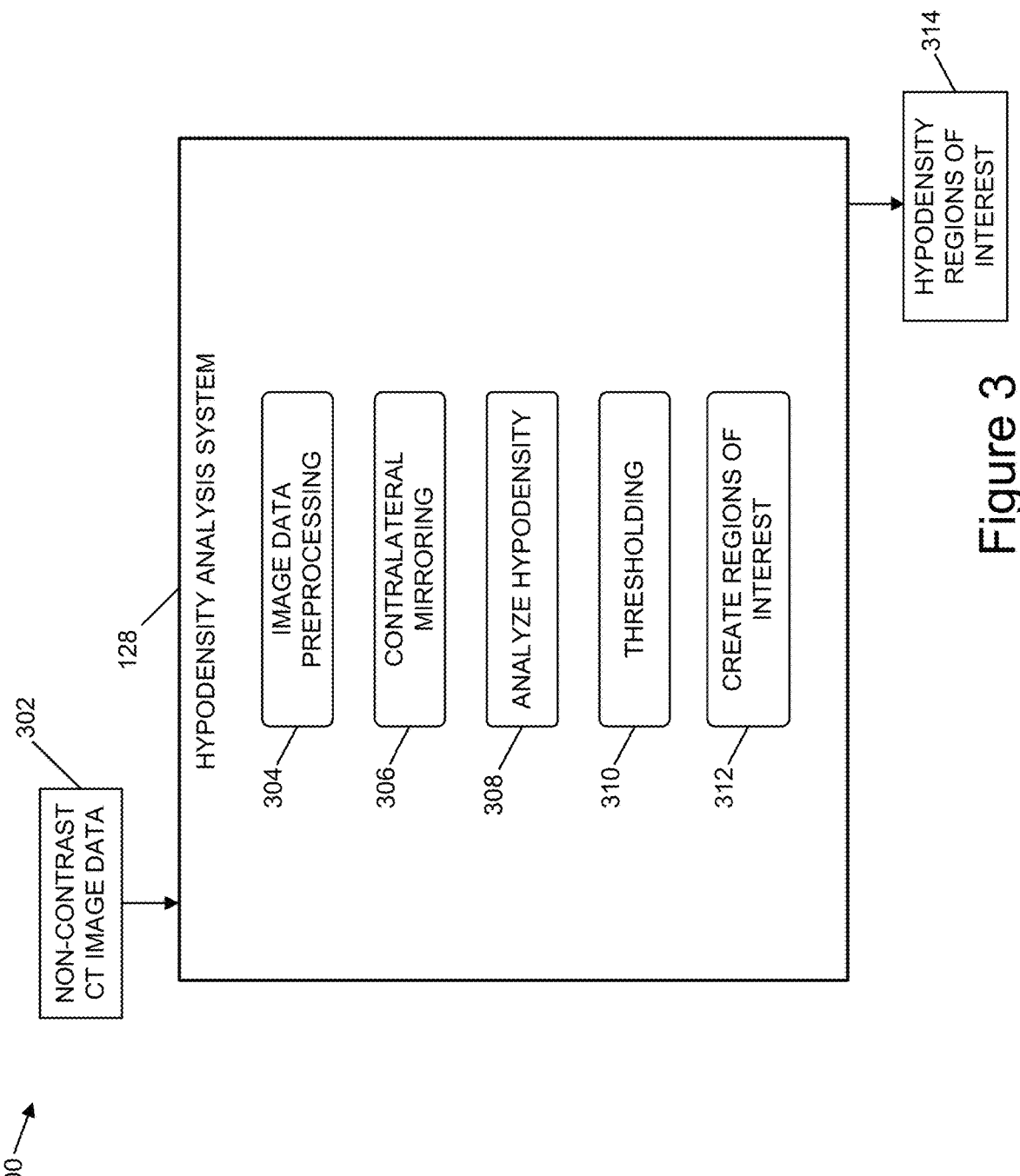
FIG. 3 is a diagrammatic representation of an example architecture to determine measures of hypodensity with respect to brain tissue, according to one or more example implementations.

In one or more illustrative examples, cerebral blood volume, cerebral blood flow, and mean tracer transit time for individual voxels can be determined using techniques related to those described in L. Ostergaard, R. M. Weiskoff, D. A. Chesler, C. Gyldensted, B. R. Rose. "*High resolution measurement of cerebral blood flow using intravascular tracer bolus passages*". Part I: Mathematical approach and statistical analysis, Magn Reson Med. 1996 November; 36(5):715-25. The values for cerebral blood volume, cerebral blood flow, and mean tracer transit time can be relative values. In one or more further illustrative examples, $T_{max}$ can be determined for individual voxels based on a maximum value of the tissue residue function for an individual time slice. Values for $T_{max}$ can be absolute values given in seconds FIG. 3 is a diagrammatic representation of an example architecture 300 to determine measures of hypodensity with respect to brain tissue, according to one or more example implementations. Areas of the brain that are hypodense can include voxels having intensity values that are less that a corresponding region of the brain in contralateral hemisphere. In one or more examples, the lower intensity values in hypodense regions can indicate an increased amount of water in the tissue that corresponds to voxels of hypodense regions.

The hypodensity analysis for CT image data can be determined using non-contrast CT image data 302. The non-contrast CT image data 302 can include a number of 2-dimensional slices that are combined to form a 3-dimensional image of a brain of a subject. In one or more examples, the non-contrast CT image data 302 can cover at least 60 mm, at least 70 mm, at least 80 mm, at least 90 mm, at least 100 mm, at least 110 mm, at least 120 mm, at least 130 mm, at least 140 mm, or at least 150 mm of the brain of the subject along the axial direction. In one or more additional examples, the non-contrast CT image data 302 can include slices having a thickness from about 0.5 mm to about 5 mm, from about 0.1 mm to about 6 mm, from about 1 mm to about 4 mm, from about 2 mm to about 5 mm, or from about 2 mm to about 6 mm. In various examples, the non-contrast CT image data 302 can have slice spacing with values similar to those of the slice thickness.

The hypodensity analysis system 128 can perform, at operation 304, one or more image data preprocessing operations can be performed with respect to the non-contrast CT image data 302. For example, in situations where the gantry is tilted during the CT scan, the data corresponding to each slice of the non-contrast CT image data 302 can be translated according to the gantry tilt to correct for the offset of the image origin produced based on the tilt of the gantry. Additionally, one or more operations can be performed to generate slices of the non-contrast CT image data 302 that have a consistent thickness. To illustrate, in various examples, the non-contrast CT image data 302 can include slices having different thicknesses due to slices at the skull base being thinner than slices that correspond to the brain tissue to minimize partial volume effects and streak artifacts. In one or more examples, the one or more preprocessing operations to generate slices having a consistent thickness can include determining a first group of slices having a first thickness and a second group of slices having a second thickness that is greater than the first thickness. In one or more illustrative examples, the first thickness can be 1, mm, 1.25 mm, 1.5 mm, 1.75 mm, 2 mm, 2.25 mm, 2.5 mm, 2.75 mm, 3 mm, 3.25 mm, or 3.5 mm and the second thickness can be 4 mm, 4.5 mm, 5 mm, 5.5 mm, 6 mm, 6.5 mm, or 7 mm. The slices included in the first group can be resampled in the axial direction to correspond to the slice spacing of the second group. Further, in situations where the slice thickness is less than a threshold thickness, a number of slices can be merged. In one or more illustrative examples, the threshold thickness for merging can be 0.5 mm, 0.75 mm, 1 mm, 1.25 mm, 1.5 mm, 2 mm, or 2.5 mm. Merging slices having a thickness that is less than the threshold thickness can improve the signal-to-noise ratio for the individual slices. The number of slices to be merged can be based on a target spacing metric between the slices. In various examples, the target spacing metric can be 2 mm, 2.5 mm, 3 mm, 3.5 mm, 4 mm, 4.5 mm, or 5 mm.

At operation 306, a contralateral mirroring operation can be performed. The contralateral mirroring operation can include operations that determine portions of the non-contrast CT image data 302 that are to be used to analyze the non-contrast CT image data 302 with respect to hypodensity. In this way, a subset of the non-contrast CT image data 302 is subjected to a hypodensity analysis in order to provide an accurate measure of hypodensity for voxels of the non-contrast CT image data 302 and to reduce the processing time to perform the hypodensity analysis. In one or more examples, the non-contrast CT image data 302 can be separated into soft tissue, ventricles, and cerebrospinal fluid by performing a co-registration process of the non-contrast CT image data 302 with the atlas utilized in the perfusion image processing system 106.

Additionally, a median intensity value of voxels included in the non-contrast CT image data 302 can be determined. The median intensity value can be a threshold intensity value used to determine voxels of the non-contrast CT image data 302 that correspond to cerebrospinal fluid. In various examples, voxels having intensity values from 0 HU to 60 HU are utilized to determine the median intensity value. The median intensity value of the voxels of the CT image data is used to determine the at least one of a location of cerebrospinal fluid, a location of an intracerebral hemorrhage, or volume effects related to bone. In one or more illustrative examples, threshold intensity values for determining cerebrospinal fluid can be from 6 HU to 15 HU, from 8 HU to 12 HU, or from 10 HU to 15 HU. In one or more additional illustrative examples, threshold intensity values for determining intracerebral hemorrhage and volume effects can be from 25 HU to 50 HU, from 35 HU to 45 HU, or from 40 HU to 50 HU. In various examples, the threshold values for determining cerebrospinal fluid, intracranial hemorrhage, and/or volume effects can be modified by an offset based on the median intensity value different from one or more threshold values. The threshold intensity value for determining cerebrospinal fluid can be used in relation to an active contour model to determine pixels of a slice that correspond to cerebrospinal fluid. In these scenarios a cerebrospinal fluid mask can be generated. The portions of the non-contrast CT image data 302 that do not correspond to cerebrospinal fluid can be used in the hypodensity analysis.

Further, a spatial correlation can be determined between soft tissue voxels (e.g., voxels that do not correspond to ventricles and cerebrospinal fluid) of a first hemisphere of the brain of the individual in relation to soft tissue voxels in the second hemisphere of the brain of the individual. In various examples, the non-contrast CT image data 302 can be mirrored on a sagittal plane and the mirrored data can be aligned with the non-contrast CT image data 302 followed by one or more non-rigid alignment processes. Ventricles and cerebrospinal fluid can be identified for both the mirrored data and the non-contrast CT image data 302. The mirrored data and the non-contrast CT image data 302 can then be slice preprocessed by median filtering and Gaussian filtering. In one or more illustrative examples, the one or more median filtering operations can be performed with a kernel radius from about 0.5 mm to about 2.5 mm, from 0.8 mm to about 1.6 mm, or from about 1.2 mm to about 2 mm, and the one or more Gaussian filtering operations can be performed with a kernel radius from about 0.2 mm to about 2 mm, from 0.4 mm to about 1.2 mm, or from about 0.5 mm to about 1.5 mm.

Determining hypodensity of brain tissue corresponding to the non-contrast CT image data 302 can be based on input data that includes the non-contrast CT image data 302 and one or more additional parameters. The one or more additional parameters can include a minimal difference in intensity values between healthy tissue and hypodense tissue in opposing hemispheres of the brain. At operation 308 a hypodensity analysis can be performed. The hypodensity analysis can include determining intensity values of voxels corresponding to a region of the brain located in a first hemisphere that can be analyzed with respect to intensity values of voxels located in a contralateral region in the second hemisphere of the brain.

A number of threshold operations can be performed at operation 310 to determine measures of hypodensity with respect to voxels undergoing the hypodensity analysis. In scenarios where a difference between the intensity values in contralateral hemispheres is greater than a threshold, a voxel can be determined to be associated with hypodense tissue. In one or more illustrative examples, the threshold difference in intensity values to identify hypodense regions can be at least 2 HU, at least 3 HU, at least 4 HU, at least 5 HU, at least 6 HU, at least 7 HU, at least 8 HU, at least 9 HU, or at least 10 HU. In one or more additional illustrative examples, the threshold difference in intensity values to identify hypodense regions can be no greater than 22 HU, no greater than 21 HU, no greater than 20 HU, no greater than 19 HU, no greater than 18 HU, no greater than 17 HU, no greater than 16 HU, no greater than 15 HU, no greater than 14 HU, no greater than 13, HU, or no greater than 12 HU. In one or more further illustrative examples, the threshold difference in intensity values to identify hypodense regions can include a number of ranges of intensity values selected from the above intensity values, such as from 2 HU to 22 HU, from 3 HU to 20 HU, from 4 HU to 18 HU, or from 5 HU to 12 HU.

The hypodensity threshold can be used, at operation 312, to generate one or more regions of interest indicating brain tissue that has been damaged and/or brain tissue having at least a threshold probability of being damaged. In one or more examples, the damaged brain tissue can be infarcted.

The hypodensity regions of interest 314 can be included in one or more insight segmentation and registration toolkit (ITK) images. The one or more ITK images can correspond to the initial non-contrast CT image data 302 that has been modified based on gantry tilt of the CT imaging device used to generate the initial CT image data. The one or more ITK images can also correspond to the initial non-contrast CT image data 302 that has been modified based on variable slice thickness in the initial CT image data and resampled to merge the modified slices having a consistent thickness. The one or more ITK images can include one or more imaging maps having two or more labels. For example, the one or more ITK images can include an imaging map that labels subacute brain tissue as "1" and that labels background and/or non-acute brain tissue as "0". Additionally, the one or more ITK images can include an imaging map with labels that indicate differences from one or more Hounsfield unit thresholds. In situations where one or more machine learning techniques are implemented, the threshold values may not be used to determine an infarct using the non-contrast CT image data.

The results of the hypodensity analysis can be utilized with respect to a mismatch analysis of the perfusion parameter data 236. The CT perfusion mismatch analysis can access the hypodensity analysis ITK files via the references included in the one or more JSON files. The non-contrast CT image data 302 can be registered with the pre-contrast agent baseline images 216 into the coordinate space of the CT perfusion image data 202. The hypodensity analysis can be integrated with mismatch outputs of the perfusion image processing system 106 to visualize regions detected in the hypodensity analysis and determine slices having hypodense regions. In scenarios where the non-contrast CT image data 302 is not obtained from a separate scan and is based on pre-contrast agent baseline images, the registration process between the non-contrast CT image data 302 and the pre-contrast agent baseline images 216 may not be performed. In situations where the non-contrast CT image data 302 is not obtained from a separate scan and is based on pre-contrast agent baseline images, the CT perfusion image data 202 can be corrected with respect to motion of the patient to avoid misregistration. The time series of images captured to generate the CT perfusion image data 202 including images captured before and after contrast agent has entered the brain of the individual can be motion corrected.

Volumes of perfusion regions of interest that correspond to brain tissue having been damaged and/or having a threshold probability of being damaged, e.g. 25% of normal CBF values, 30% of normal CBF values, 35% of normal CBF values, or 40% of normal CBF values, and volumes of hypodense regions on NCCT (or pre-contrast baseline CT scans) can be determined by computing the voxels included in a labeled region of a labeled image and multiplying the number of voxels by the volume of a single voxel. In situations where multiple regions are overlapping that indicate different degrees of hypodensity, different amounts of tissue damage, and/or different probabilities of tissue damage being present, the larger region can include the volume of the smaller region that is within the larger region. For example, in situations where a first region includes a second region, the volume of the first region can include the voxels corresponding to the first region and the volume of the second region.

Mismatch ratios and volumes can be determined that indicate differences between volumes of regions perfusion images with respect to different perfusion parameters. Mismatch ratios and mismatch volumes can correspond to an amount of brain tissue that may be at risk for becoming damaged if blood flow continues to be disrupted to the brain tissue. In one or more illustrative examples, for CT perfusion, the mismatch ratio can be determined by:

$$mismatch\,ratio = \frac{ROIvolume(Tmax > th1)}{ROIvolume(rCBF < th2)},$$

and mismatch volume can be determined by $$mismatch\,volume = ROIvolume(T_{max} > th1) - ROI\,(rCBF < th2)$$

where th is a threshold value for a given region.

In one or more examples, the th1 value for $T_{max}$ can be at least 4 seconds, at least 6 seconds, at least 8 seconds, or at least 10 seconds. Further, the th2 values for relative cerebral blood flow (rCBF) can be less than 20%, less than 30%, less than 34%, or less than 38%. In various examples, the th value for relative cerebral blood volume (rCBV) can be less than 34%, less than 38%, or less than 42%. In one or more illustrative examples, the threshold values, th1 and th2, can be arbitrarily chosen at the discretion of a healthcare practitioner.

Although the illustrative example of FIG. 3 is directed to one or more example implementations to perform a hypodensity analysis with respect to non-contrast CT image data, different implementations can also be used to determine the hypodensity regions of interest. For example, as described with respect to FIG. 1 and the hypodensity analysis system 128, machine learning techniques can be implemented to determine the hypodensity regions of interest.

Figure 4:
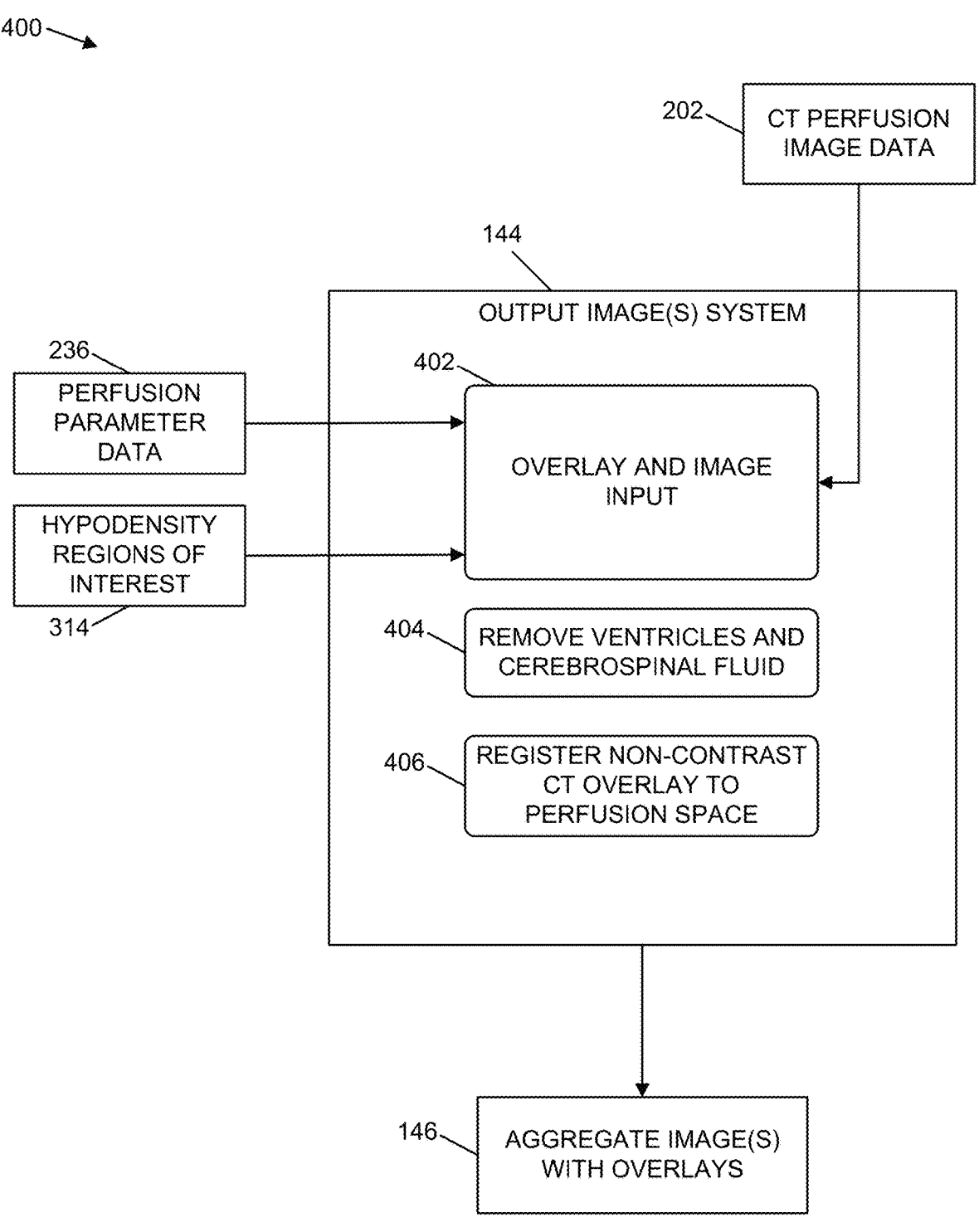
FIG. 4 is a diagrammatic representation of an example architecture to aggregate information generated from different imaging modalities to determine an amount of damage to brain tissue, in accordance with one or more example implementations.

FIG. 4 is a diagrammatic representation of an example architecture 400 to aggregate information generated from different imaging modalities to determine an estimate of the extent of irreversible brain tissue damage, in accordance with one or more example implementations. The architecture 400 can include the output image system 144. At operation 402, the output image system 144 can obtain the perfusion parameter data 236 and the hypodensity regions of interest 314 as well as the CT perfusion image data 202. The output image system 144 can, at operation 404, remove portions of the CT perfusion image data 202 that correspond to the ventricles and the cerebrospinal fluid. The output image system 144 can also, at operation 406, register the hypodensity regions of interest derived from the non-contrast CT image data 302 and the regions of interest identified by the perfusion image processing system 106 based on the CT perfusion image data 202. In various examples, the output image system 144 can generate the one or more aggregate images 146 based on the regions of interest derived from the hypodensity analysis performed by the hypodensity analysis system 128 and the regions of interest derived from the analysis of the CT perfusion image data 202 by the perfusion image processing system 106. To illustrate, the one or more aggregate images 146 can include a first overlay indicating the regions of interest derived from the CT perfusion image data 202 by the perfusion image processing system 106 and a second overlay indicating the regions of interest derived from the hypodensity analysis performed by the hypodensity analysis system 128. The first overlay and the second overlay can be displayed over one or more slices of the CT perfusion image data 202.

Although the illustrative example of FIG. 4 is directed to one or more example implementations to generate an overlay indicating regions of interest of a brain of an individual that may be damaged, additional implementations can also be performed. Different portions of the CT perfusion image data 202 can be removed other than the portions corresponding to the ventricles and cerebrospinal fluid or the portions of the CT perfusion image data 202 corresponding to the ventricles and cerebrospinal fluid can remain. Additionally, the perfusion regions of interest and the hypodensity regions of interest can be identified and combined prior to being provided to the output image system 144.

Figure 5:
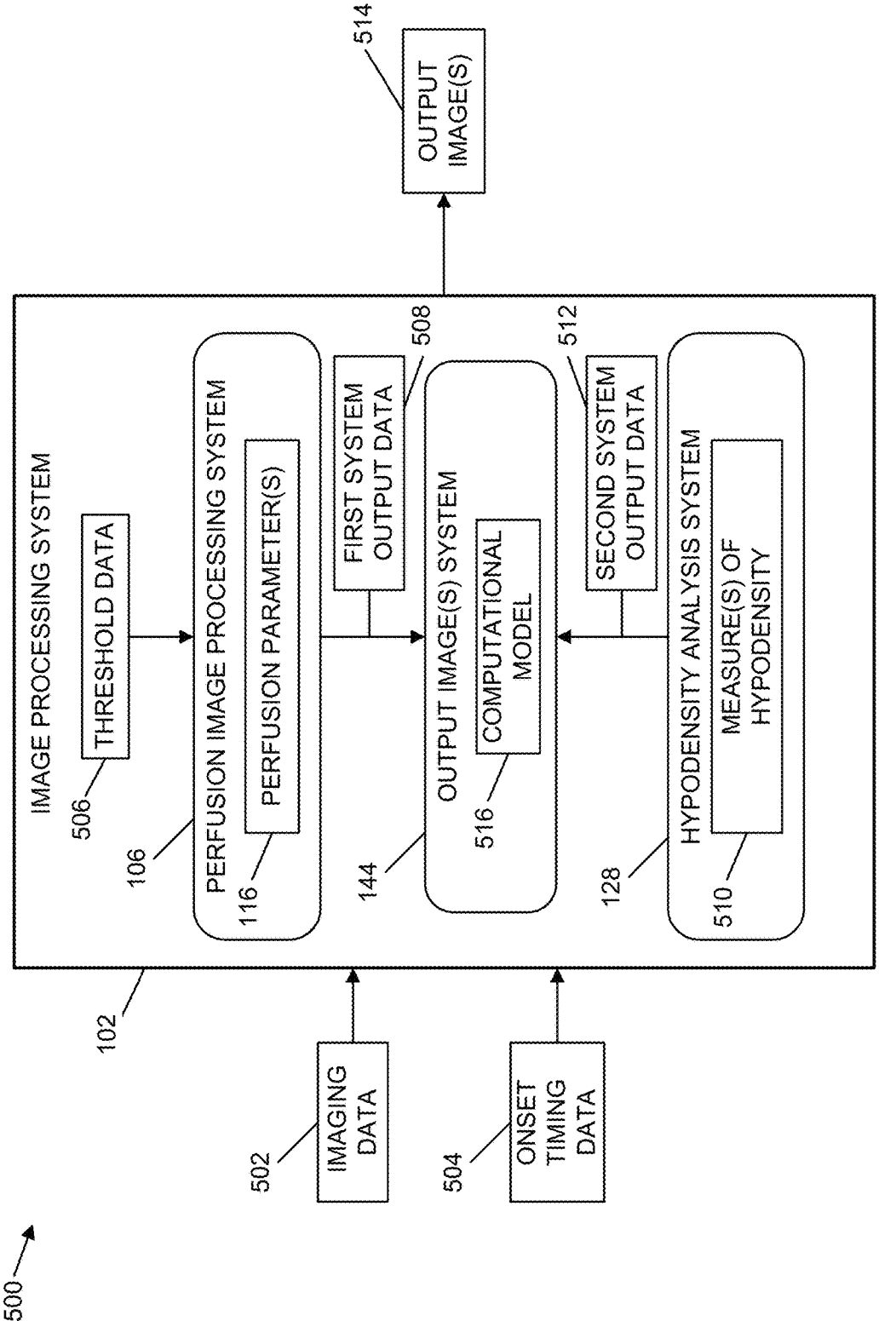
FIG. 5 is a diagrammatic representation of an example architecture to generate image data indicating an amount of damage to brain tissue based on timing of onset of a biological condition corresponding to one or more vessels of brains of individuals, in accordance with one or more example implementations.

FIG. 5 is a diagrammatic representation of an example architecture 500 to generate image data indicating an amount of damage to brain tissue based on timing of onset of a biological condition corresponding to one or more vessels of a brain of an individual, in accordance with one or more example implementations. The image processing system 102 may obtain imaging data 502. The imaging data 502 may be obtained from one or more imaging data sources. The one or more imaging data sources may implement one or more imaging techniques to generate the imaging data 502.

In one or more examples, the imaging data 502 may include first imaging data that is generated by implementing a first imaging technique. The first imaging technique can be a perfusion-based imaging technique. In one or more illustrative examples, the first imaging technique can be a computed tomography (CT) based imaging technique. In one or more additional illustrative examples, the first imaging technique can be a CT-perfusion based imaging technique. In one or more additional illustrative examples, the first imaging technique can be a CT-angiography based imaging technique.

Additionally, the imaging data 502 can include second imaging data that can be generated by a second imaging technique. The second imaging technique can be a non-perfusion-based imaging technique. In various examples, the second imaging technique can be a non-contrast agent-based imaging technique. In one or more illustrative examples, the second imaging technique can implement one or more non-contrast CT imaging techniques.

In various examples, the imaging data 502 can correspond to one or more images of a brain of an individual captured by a CT imaging apparatus over a period of time, such that a series of images of the brain can be captured in succession over the period of time. Individual images in the series of images can be referred to herein as "slices.". The imaging data can include images of the brain of an individual that indicate the brain before the contrast agent is delivered and additional images of the brain of the individual that indicate the presence of the contrast agent in one or more regions of the brain.

The imaging data 502 can indicate intensity values of voxels of the images captured of the brains of individuals. The intensity values can be indicated in Hounsfield units. In one or more examples, the intensity values of voxels that correspond to regions of the brain in which the contrast agent is present can be greater than the intensity values of voxels that correspond to regions of the brain in which the contrast agent is not present. In various examples, intensity values of voxels included in the imaging data 502 can indicate an amount of contrast agent present in regions of brains of individuals. In one or more illustrative examples, the imaging data 502 can be formatted according to a Digital Imaging and Communications in Medicine (DICOM) standard. In various examples, the imaging data 502 can include at least one of the first imaging data 108 of FIG. 1 or the second imaging data 130 of FIG. 1. The image processing system 102 can also obtain onset timing data 504. The onset timing data 504 can indicate an amount of time elapsed since a biological condition became present within a brain of an individual. In one or more examples, the onset timing data 504 can indicate a period of time from minutes to hours. For example, the onset timing data 504 can be from 1 minute to 48 hours, from 10 minutes to 40 hours, from 30 minutes to 36 hours, from 1 hour to 30 hours, from 2 hours to 24 hours, from 30 minutes to 12 hours, from 1 hour to 12 hours, from 15 minutes to 6 hours, or from 15 minutes to 4 hours. In one or more illustrative examples, the onset timing data 504 can indicate an amount of time elapsed since a biological condition was detected within a brain of an individual. In one or more additional illustrative examples, the onset timing data 504 can indicate an amount of time elapsed since one or more symptoms of a biological condition were detected in an individual. In various examples, the biological condition can reduce the flow of blood to one or more regions of the brain of an individual. In at least some examples, the biological condition can be related to one or more vessels of the brain of the individual. To illustrate, the biological condition can include a stroke.

In one or more examples, the onset timing data 504 can be captured via one or more input devices of one or more computing devices. For example, the onset timing data 504 can be captured via one or more user interfaces displayed by a computing device. Additionally, the onset timing data 504 can be captured via one or more audio input devices, such as one or more microphones of a computing device. In one or more illustrative examples, the onset timing data 504 can be captured by a computing device of a healthcare practitioner. In one or more further illustrative examples, the onset timing data 504 can be captured by a computing device of an individual in which the biological condition is present. In various examples, the onset timing data 504 can be determined based on an analysis of the imaging data 502.

The image processing system 102 can include the perfusion image processing system 106. The perfusion image processing system 106 can analyze the imaging data 502 and generate the one or more perfusion parameters 116 for one or more voxels of the imaging data 502. For example, the perfusion image processing system 106 can analyze the intensity values of voxels of the imaging data 502 with respect to one or more regions of the brain to determine the one or more perfusion parameters 116. The one or more perfusion parameters 116 can indicate a flow of blood through one or more regions of the brain of an individual. In one or more illustrative examples, the perfusion parameters 116 can include at least one of a measure of cerebral blood flow (CBF), a measure of cerebral blood volume (CBV), a measure of mean tracer transit time (MTT), or $T_{max}$ that corresponds to an amount of the contrast agent that entered a voxel remains inside the voxel at a later time.

The perfusion image processing system 106 can analyze the one or more perfusion parameters 116 in conjunction with the imaging data 502 to determine one or more regions of the brain that have been damaged tissue due to a disrupted supply of blood to the one or more regions. For example, the perfusion image processing system 106 can analyze the one or more perfusion parameters 116 and intensity values of voxels corresponding to blood vessels of the brain of an individual to determine an extent of the disruption of the flow of blood to one or more regions of the brain of the individual. In one or more examples, the one or more perfusion parameters 116 can be analyzed to determine an amount of time of disruption to the flow of blood to a region of the brain of an individual. In one or more illustrative examples, the perfusion image processing system 106 can analyze the imaging data 502 to determine a least a portion of the onset timing data 504. Based on the extent of the disruption of blood flow to one or more regions of the brain of an individual, the perfusion image processing system 106 can determine one or more regions of interest having at least a threshold probability of having damaged tissue.

In one or more examples, the perfusion image processing system 106 can utilize threshold data 506 to determine one or more regions of the brain of an individual in which damaged tissue may be present. In one or more illustrative examples, the threshold data 506 can indicate threshold levels of one or more of the perfusion parameters 116. The threshold levels can indicate values of the perfusion parameters 116 that correspond to damaged tissue in a region of the brain of an individual. In various examples, the threshold levels can indicate values of the perfusion parameters 116 that correspond to at least a minimum probability that tissue in a region of the brain of an individual has been damaged. In at least some examples, the threshold data 506 can include one or more threshold values for at least one of cerebral blood flow, cerebral blood volume, MTT, or $T_{max}$.

The threshold data 506 utilized by the perfusion image processing system 106 can be based on the onset imaging data 504. For example, as the period of time from onset of a biological condition that disrupts blood flow to one or more regions of the brain of an individual changes, one or more threshold values used by the perfusion image processing system 106 can also change. In one or more examples, as the period of time from onset of the biological condition increases, one or more threshold values of one or more perfusion parameters can also increase. In various examples, for a first period of time from onset of a biological condition that disrupts blood flow to one or more regions of the brain of an individual to a current time, one or more first threshold values can be used by the perfusion image processing system 106 to determine whether damage has occurred with respect to the one or more regions of the brain of the individual. Additionally, for a second period of time from onset of the biological condition, one or more second threshold values can be used by the perfusion image processing system 106 to determine whether damage has occurred with respect to the one or more regions of the brain of the individual.

In one or more illustrative examples, a first period of time from onset of a biological condition that disrupts blood flow to one or more regions of the brain of an individual can be no greater than 30 minutes, no greater than 1 hour, no greater than 2 hours, no greater than 4 hours, or no greater than 6 hours. In these scenarios, an illustrative example of a threshold value of a perfusion parameter 116 related to the first period of time can be a cerebral blood flow value that is less than 10% of a standard cerebral blood flow value, less than 15% of a standard cerebral blood flow value, less than 20% of a standard cerebral blood flow value, or less than 25% of a standard cerebral blood flow value, or less than 30% of a standard blood flow value. In one or more examples, the standard cerebral blood flow value can be determined using information from the individual from which the imaging data 502 was captured. The standard cerebral blood flow value can also be determined using information from a number of individuals. In various examples, the standard cerebral blood flow value can be an average cerebral blood flow value based on an analysis of cerebral blood flow values for a number of individuals. In at least some examples, the standard cerebral blood flow value can be based on an age of an individual. In one or more additional examples, the standard cerebral blood flow value can be based on blood value values of one or more vessels included in one or more regions of the brain of an individual. In one or more further examples, the standard cerebral blood flow value can be based on diameters of blood vessels.

In one or more additional illustrative examples, a second period of time from onset of the biological condition can be greater than the threshold values associated with the first period of time. To illustrate, a second period of time from onset of the biological condition that disrupts blood flow to one or more regions of the brain of an individual can be at least 30 minutes, at least 1 hour, at least 2 hours, at least 4 hours, or at least 6 hours. In one or more examples, the second period of time can also have an upper limit, such as no greater than 48 hours, no greater than 36 hours, no greater than 24 hours, no greater than 18 hours, no greater than 12 hours, no greater than 10 hours, no greater than 8 hours, no greater than 6 hours, or no greater than 4 hours depending on the lower bound of the second period of time. In various examples, the threshold value for a blood flow parameter related to the second period of time can be greater than the threshold for a blood flow parameter related to the first period of time. To illustrate, an illustrative example of a threshold value of a perfusion parameter 116 for the second period of time can be a cerebral blood flow value that is less than 25% of a standard cerebral blood flow value, less than 30% of a standard cerebral blood flow value, less than 35% of a standard cerebral blood flow value, less than 40% of a standard cerebral blood flow value, less than 45% of a standard cerebral blood flow value, or less than 50% of a standard cerebral blood flow value. In various examples, the threshold value for a blood flow parameter related to the second period of time can be greater than the threshold for a blood flow parameter related to the first period of time. In still other examples, the threshold value for a blood flow parameter related to the second period of time can be less than the threshold for a blood flow parameter related to the first period of time. In situations where the blood flow parameter includes at least one of cerebral blood flow, cerebral blood volume, MTT, or $T_{max}$, the threshold value for the first period of time can be less than the threshold value for the second period of time because as the time from the onset of a biological condition disrupting blood flow to a region of the brain of an individual increases, the likelihood of reperfusion taking place with respect to the region. Thus, the blood flow to a region of the brain of the individual can be relatively low in early stages of a biological condition causing disruption of blood flow to the region, such as a stroke, while in the later stages of the biological condition, the blood flow may have increased from vessels other than a vessel that used to have or currently has restricted blood flow.

The perfusion image processing system 106 can generate first system output data 508. The first system output data 508 can include values of one or more of the perfusion parameters 116. The first system output data 508 can also indicate a probability of damage to one or more regions of a brain of an individual. In addition, the first system output data 508 can include overlay imaging data that corresponds to an overlay indicating a region of the brain of an individual in which tissue damage is present or has at least a threshold probability of being present. In various examples, the perfusion image processing system 106 can execute one or more computational models to determine at least one of values of one or more of the perfusion parameters 116 or the first system output data 508. In one or more illustrative examples, the perfusion image processing system 106 can execute one or more machine learning techniques to generate at least one of values of one or more of the perfusion parameters 116 or the first system output data 508.

The image processing system 102 can also include the hypodensity analysis system 128. The hypodensity analysis system 128 can analyze the intensity values of voxels of the imaging data 502 with respect to one or more regions of the brain of an individual to determine one or more measures of hypodensity 510. The one or more measures of hypodensity can be expressed as Hounsfield density values. In one or more examples, the one or more measures of hypodensity 510 can be determined to identify one or more regions of the brain of an individual in which tissue damage is present. In various examples, the hypodensity analysis system 128 can analyze intensity values of voxels included in the imaging data 502 to determine regions of the brain of the individual that have at least a threshold probability of being damaged. In one or more additional examples, the hypodensity analysis system 128 can analyze voxels in different hemispheres of the brain of an individual to determine one or more regions of the brain that include hypodensity tissue. In one or more illustrative examples, the hypodensity analysis system 128 can also implement one or more machine learning techniques to determine regions of hypodense tissue in the brain of an individual.

The onset timing data 504 can be analyzed by the hypodensity analysis system 128 to determine a likelihood of tissue damage being present in a region of the brain of an individual. In one or more examples, a likelihood of tissue damage being present in a region of the brain of an individual may increase as a time from onset of a biological condition with respect to one or more vessels of the brain of an individual increases. In one or more scenarios, at least one of the accuracy or the precision of results generated by the hypodensity analysis system 128 can increase as the time from onset of the biological condition increases. That is, hypodense tissue in the brain of the individual can be detected with greater confidence as the time from onset of the biological condition increases. Thus, the hypodensity analysis system 128 can determine one or more regions of the brain of an individual in which tissue damage is present and a likelihood score that corresponds to a likelihood of the tissue damage being present. In one or more illustrative examples, the hypodensity analysis system 128 can generate second system output data 512 that indicates one or more regions of the brain of an individual in which tissue damage is present. The hypodensity analysis system 128 can also generate a likelihood that the measures of hypodensity 510 generated using the imaging data 502 indicate tissue damage in the one or more regions.

One or more computational models can be executed to determine a likelihood with respect to the measures of hypodensity 510 indicating that tissue damage is present in a brain of an individual. In various examples, the hypodensity analysis system 128 can execute one or more machine learning algorithms to determine a likelihood with respect to the measures of hypodensity 510 indicating that tissue damage is present in the brain of an individual. For example, one or more machine learning classification algorithms can be executed to determine a likelihood with respect to the measures of hypodensity 510 indicating that tissue damage is present in a brain of an individual. In one or more illustrative examples, one or more random forests algorithms can be executed to determine a likelihood with respect to the measures of hypodensity 510 indicating that tissue damage is present in a brain of an individual. In one or more further illustrative examples, a likelihood of tissue damage being present with respect to the measures of hypodensity 510 indicating that tissue damage is present in a brain of an individual can be based on a number of branches of the output of one or more random forests algorithms indicating tissue damage to the region of the brain of the individual.

In one or more illustrative examples, the hypodensity analysis system 128 can analyze the imaging data 502 for the brain of an individual during a first period of time since onset of the biological condition and determine first measures of hypodensity 510. The hypodensity analysis system 128 can determine, based on the first measures of hypodensity 510, one or more regions of the brain of the individual in which tissue damage is present. The hypodensity analysis system 128 can also determine, based on the onset timing data, a likelihood of the first measures of hypodensity 510 indicating that tissue damage is present in the one or more regions. In scenarios where the likelihood is less than a threshold likelihood, the hypodensity analysis system 128 can indicate in the second system output data 512 that tissue damage is not present in the one or more regions. Additionally, in situations where the likelihood is at least a threshold likelihood, the hypodensity analysis system 128 can indicate in the second system output data 512 that tissue damage is present in the one or more regions.

The hypodensity analysis system 128 can also analyze the imaging data 502 for the brain of an individual during a second period of time since onset of the biological conditions and determine second measures of hypodensity. The second period of time can be subsequent to the first period of time. In various examples, the hypodensity analysis system 128 can determine, based on the onset timing data 504, an additional likelihood that the second measures of hypodensity 510 indicate that tissue damage is present in at least the one or more regions. In situations where the additional likelihood is less than a threshold likelihood, the hypodensity analysis system 128 can indicate in the second system output data 512 that tissue damage is not present in the one or more regions. Additionally, in situations where the additional likelihood is at least a threshold likelihood, the hypodensity analysis system 128 can indicate in the second system output data 512 that tissue damage is present in the one or more regions. In one or more illustrative examples, the additional likelihood determined based on the second measures of hypodensity can be greater than the initial likelihood determined based on the first measures of hypodensity.

The image processing system 102 can include the output image system 144. The output image system 144 can analyze the first system output data 508 and the second system output data 512 to determine one or more output images 514. In one or more examples, the output images system 144 can execute one or more computational models 516 to generate the one or more output images 514. In one or more examples, the output images system 144 can execute the one or more computational models 516 with respect to the first system output data 508 to determine a first region of the brain of an individual in which tissue damage is present. Additionally, the output images system 144 can execute the one or more computational models 516 with respect to the second system output data 512 to determine a second region of the brain of the individual in which tissue damage is present. In various examples, the second region can overlap at least a portion of the first region. Further, the second region can include portions of the brain of the individual that are not included in the first region.

In one or more illustrative examples, the output image system 144 can generate an aggregate image based on the first region and the second region. The aggregate image can include a first overlay that corresponds to the first region and a second overlay that corresponds to the second region. In one or more implementations, the one or more computational models 516 can be executed based on a likelihood included in the second system output data 512 that is related to the second region. In one or more scenarios, the one or more computational models 516 can determine that the second region is not to be included in the aggregate image based on the likelihood value. In one or more additional examples, the one or more computational models 516 can determine that a portion of the second region is not to be included in the aggregate image based on the likelihood value. In one or more further examples, the second region or at least a portion of the second region may not be included in the aggregate image based on an indication included in the second system output data 512 to exclude at least a portion of the second region from the aggregate image. The indication can be determined based on a likelihood value generated by the hypodensity analysis system 128 in relation to the measures of hypodensity 510 corresponding to damaged tissue in the second region. The one or more output images can include at least one of the first region and at least a portion of the second region overlaid on an image included in the imaging data 502. For example, the one or more output images 514 can include one or more CT-images of the brain of an individual with contrast agent present in conjunction with one or more overlays indicating one or more regions of the brain of the individual in which damaged tissue is present. In one or more additional examples, the one or more output images 514 can include one or more non-contrast CT images of the brain of the individual in which damaged tissue is present. In one or more further examples, the one or more output images 514 can include at least a first CT image of the brain of the individual with contrast agent present and at least a second non-contrast CT image of the brain of the individual in conjunction with one or more overlays indicating regions of the brain of the individual in which damaged tissue is present or has at least a threshold probability of being present. In at least some examples, a CT image included in the one or more output images 514 can have one or more overlays that are different from one or more overlays with respect to a non-contrast CT image included in the one or more output images 514. In one or more scenarios, the one or more overlays of perfusion-based CT can correspond to one or more regions determined by the perfusion image processing system 106 to have tissue damage present. The one or more overlays of the non-contrast CT images can correspond to one or more regions determined by the hypodensity analysis system 128 to have tissue damage present.

Figure 7:
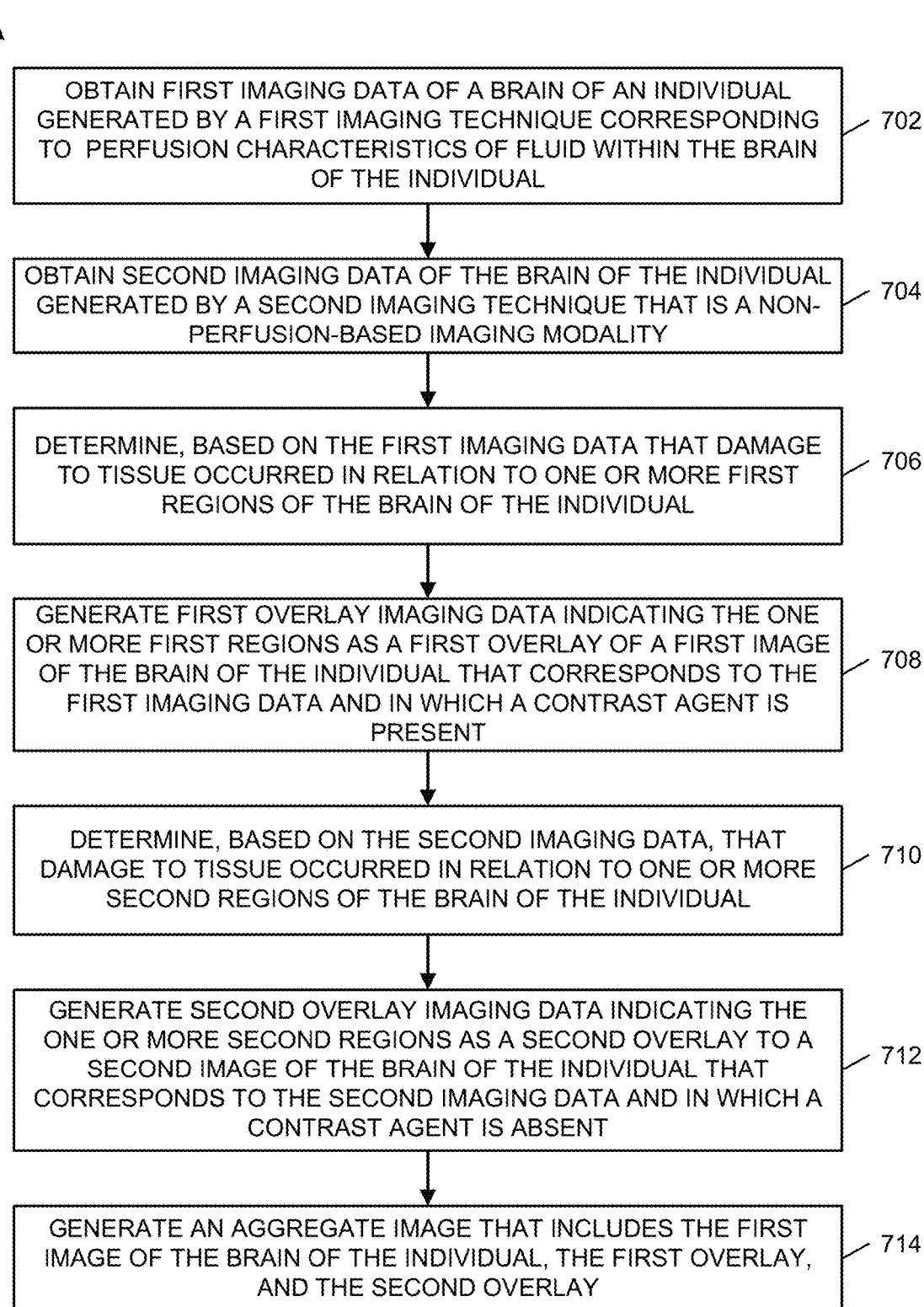
FIG. 7 is a flowchart illustrating example operations of a process to determine perfusion parameters and measures of hypodensity with respect to brain tissue to determine a potential amount of damage to at least a portion of the brain tissue, according to one or more example implementations.

FIGS. 6-8 illustrate flowcharts of processes to generate images that indicate brain tissue that has been damaged. The processes may be embodied in computer-readable instructions for execution by one or more processors such that the operations of the processes may be performed in part or in whole by the functional components of the image processing system 102. Accordingly, the processes described below are by way of example with reference thereto, in some situations. However, in other implementations, at least some of the operations of the processes described with respect to FIG. 6-8 may be deployed on various other hardware configurations. The processes described with respect to FIGS. 6-8 are therefore not intended to be limited to the image processing system 102 and can be implemented in whole, or in part, by one or more additional components. Although the described flowcharts can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

FIG. 6 is a flowchart illustrating example operations of a process 600 to determine an aggregate image based on image data generated by different imaging modalities and to generate overlays of the aggregate image indicating a potential amount of damage to brain tissue, according to one or more example implementations. At operation 602, the process 600 can include obtaining first imaging data for a brain of an individual. In one or more examples, the first imaging data may be generated by a first imaging technique. The first imaging technique can be related to perfusion characteristics of fluid within the brain of the individual. In various examples, the first imaging technique can generate images of the brain of the individual that indicate the presence of blood within blood vessels of the brain of the individual. In one or more illustrative examples, the first imaging technique can comprise a computed tomography perfusion imaging technique. In one or more additional examples, the first imaging technique can include a computed tomography angiography imaging technique.

In addition, the process 600 can include, at operation 604, obtaining second imaging data. In one or more examples, the second imaging data may be generated by a second imaging technique that is a non-perfusion-based imaging technique. In one or more illustrative examples, the second imaging technique can comprise a non-contrast computed tomography imaging technique. In one or more additional illustrative examples, the second imaging technique can include a diffusion-based magnetic resonance imaging technique. The second imaging data can include a number of second slices captured in succession over a second period of time. Individual second slices can include a cross-section of a portion of the brain of the individual. In various examples, the first imaging data and the second imaging data can be generated by different imaging apparatuses. The first imaging data and the second imaging data can also be generated using a same imaging apparatus. Further, in one or more examples, the first imaging data and the second imaging data can be generated during different periods of time. In at least some examples, the different periods of time may not be overlapping.

In various examples, the first imaging data and the second imaging data can be captured using a same imaging modality at different times. For example, the first imaging data can be captured using an imaging technique during a period of time when a contrast agent is present in the brain of the individual. Additionally, the second imaging data can be captured using the imaging technique during a period of time when the contrast agent is not present in the brain of the individual. In one or more illustrative examples, the imaging technique can include a computed tomography perfusion imaging technique that captures images of the brain before a contrast agent is delivered to the individual and captures images of the brain of the individual after the contrast agent is delivered to the individual. In one or more illustrative examples, the first imaging data can include a number of first slices captured in succession over a first period of time and the second imaging data can include a number of second slices captured in succession over a second period of time. Individual first slices and second slices can include a cross-section of a portion of the brain of the individual.

The process 600 can also include, at operation 606, determining one or more perfusion parameters based on first intensity values of first voxels of the first imaging data. The one or more perfusion parameters can indicate the flow of blood in the brain of the individual. The one or more perfusion parameters can be generated for individual voxels included in the first imaging data. In one or more example, the number of voxels for which the one or more perfusion parameters are determined can correspond to brain tissue. In various examples, the first imaging data can be analyzed to identify voxels included in the first imaging data that correspond to brain tissue. In one or more illustrative examples, voxels that correspond to brain tissue within the first imaging data can be determined by analyzing intensity values of the voxels. Additionally, voxels that correspond to brain tissue within the first imaging data can be determined based on an atlas that indicates a number of regions of the brain where at least a portion of the first imaging data is aligned with the atlas.

The process 600 can also include, at operation 608, determining, based on the one or more perfusion parameter, that damage to tissue occurred in one or more first regions of the brain of the individual. In one or more examples, one or more perfusion parameters for one or more regions of interest can be analyzed in relation to one or more threshold values. In various examples, the one or more threshold values can correspond to values of the one or more perfusion parameters that have been previously determined to correspond to brain tissue damage. In various examples, the one or more threshold values can correspond to probabilities of damage being present in brain tissue, such as at least a 50% probability of damage being present in brain tissue, at least a 60% probability of damage being present in brain tissue, at least a 70% probability of damage being present in brain tissue, at least an 80% probability of damage being present in brain tissue, at least a 90% probability of damage being present in brain tissue, at least a 95% probability of damage being present in brain tissue, or at least a 99% probability of damage being present in brain tissue. In one or more illustrative examples, the one or more perfusion parameters can include cerebral blood flow. Measures of cerebral blood flow can be determined by analyzing intensity values of voxels included in the first imaging data. Measures of cerebral blood flow for voxels corresponding to one or more regions of the brain of the individual can be analyzed with respect to one or more measures of cerebral blood flow. In scenarios where voxels of a region of the brain of the individual are associated with measures of cerebral blood flow that correspond to one or more threshold values, a determination can be made of at least a threshold probability that tissue damage is present in the region of the brain of the individual.

Further, the process 600 can include, at operation 610, determining one or more second regions of the brain that correspond to one or more portions of the brain tissue having a measure of hypodensity that corresponds to a threshold measure of hypodensity. The measure of hypodensity can be determined based on intensity values of voxels included in the one or more second regions. The threshold measure of hypodensity can correspond to a measure of hypodensity that is associated a probability of brain tissue damage based on previously analyzed intensity values of voxels included images generated using non-contrast computed tomography imaging techniques.

Additionally, at operation 612, the process 600 can include generating an aggregate image that includes a first overlay indicating the one or more first regions and a second overlay that includes the one or more second regions. In one or more examples, the aggregate image can correspond to an individual slice of a plurality of slices included in the first imaging data. In these scenarios, the aggregate image can include a slice of a plurality of slices captured by perfusion-based computed tomography imaging techniques. In various examples, the aggregate image can be included in a user interface. In one or more illustrative examples, user interface data can be generated that corresponds to the user interface. The user interface can also display multiple slices included in the first imaging data. At least a portion of the individual slices can include a respective first overlay that corresponds to one or more regions of brain tissue displayed by the individual slice that have been damaged or that have at least a threshold probability of being damaged according to values of one or more perfusion parameters. Additionally, at least a portion of the individual slices can include a respective second overlay that corresponds to one or more regions of brain tissue displayed by the individual slice that have been damaged or that have at least the threshold probability of being damaged according to hypodensity values of the one or more regions.

FIG. 7 is a flowchart illustrating example operations of a process 700 to determine perfusion parameters and measures of hypodensity with respect to brain tissue to determine the extent of irreversibly damaged brain, according to one or more example implementations. At operation 702, the process 700 can include obtaining first imaging data of a brain of an individual generated by a first imaging technique corresponding to perfusion characteristics within the brain of the individual. In one or more illustrative examples, the first imaging technique can comprise a computed tomography perfusion imaging technique.

In addition, the process 700 can include, at operation 704, obtaining second imaging data generated by a second imaging technique that is a non-perfusion-based imaging technique. In one or more illustrative examples, the second imaging technique can comprise a non-contrast computed tomography imaging technique. The second imaging data can include a number of second slices captured in succession over a second period of time. Individual second slices can include a cross-section of a portion of the brain of the individual.

The process 700 can also include, at operation 706, determining, based on the first imaging data, that damage to tissue occurred in relation to one or more first regions of the brain of the individual. In one or more examples, prior to determining the one or more first regions, the first imaging data can be corrected for motion of the individual during the capture of the first imaging data. For example, the first imaging data includes a number of first slices captured in succession over a period of time. One or more of the first slices can be determined that are offset from a reference image by at least a threshold amount in response to motion of the individual during capture of the first imaging data. In various examples, a registration process can be performed to align the one or more first slices with the reference image. One or more motion correction parameters can be determined based on the registration process. The one or more motion correction parameters can include at least one of one or more rotational parameters or one or more translational parameters that position voxels of the one or more first slices within a threshold distance of corresponding voxels of the reference image.

In one or more additional examples, the first imaging data can undergo a time correction process. The time correction process can include determining that a portion of the first slices is captured at a time interval that differs from an additional time interval between the capture of an additional portion of the first slices. Further, the time correction process can include modifying the time interval and the additional time interval to be a common time interval such that the first slices are arranged with a common time interval between successive first slices.

In various examples, determining the one or more first regions having tissue damage can include determining a number of perfusion parameters. In one or more examples, the perfusion parameters can be determined based on baseline intensity values of voxels prior to the arrival of contrast agent to the voxels. In order to determine the baseline intensity values, a portion of the first imaging data that is captured prior to the arrival of contrast agent to the voxels can be determined. For example, changes in intensity values of at least a portion of the voxels included in the first imaging data over a period time can be determined and based on the changes in intensity values, a time that the contrast agent entered a portion of the brain of the individual can be determined. That is, prior to the arrival of the contrast agent, the intensity values of voxels can be less than intensity values of the voxels in which contrast agent is present. After determining an arrival time of contrast agent in voxels included in individual slices of the first imaging data, the image of the brain of the individual in which the contrast agent is absent based on portions of the first imaging data captured prior to the arrival time can be generated.

In addition, determining the one or more first regions of the brain having damaged brain tissue can include performing a registration process between at least a portion of the first imaging data and an anatomical template of a human head and generating a deformation field as a result of the registration process. The deformation field can indicate an extent that the voxels included in the first imaging data are to be transformed in order to align with the anatomical template. After alignment with the anatomical template, various regions of the brain of the individual can be identified with respect to the first imaging data. For example, the deformation field can be applied to an atlas that indicates a number of regions of a human brain to produce a modified atlas that corresponds to the brain of the individual. In this way, portions of the first imaging data that correspond to regions of the brain that are not used to determine the one or more perfusion parameters can be removed. To illustrate, respective regions included in the modified atlas can be used to determine individual regions of the brain of the individual and one or more portions of the first imaging data can be removed that do not correspond to the brain tissue. As a result, modified first imaging data is generated that corresponds to brain tissue without other parts of the body of the individual that may be captured in the first imaging data, such as the skull or eyes.

The one or more perfusion parameters can be determined based on the intensity values of voxels related to the brain tissue of the individual and the intensity values can be indicated by a contrast agent concentration curve for individual voxels. In one or more examples, a contrast agent concentration curve can be determined for individual voxels included in the modified first imaging data based on intensity values of the individual voxels over time with respect to one or more reference intensity values. In various examples, an intensity value of a voxel included in the modified first imaging data that has greater than a threshold difference with at least one reference value of the one or more reference values indicates that the contrast agent is present in the voxel.

In various examples, an arterial input function and a venous output function can be used to determine the one or more perfusion parameters. In one or more examples, one or more first candidate regions for the arterial input function of the modified first imaging data that include a first blood vessel having at least a threshold diameter based on one or more first locations of first blood vessels having the threshold diameter in the modified atlas can be determined. The one or more first candidate regions can include at least a portion of the middle cerebral artery or at least a portion of the anterior cerebral artery. The arterial input function can be generated based on first contrast agent concentration curves for first voxels included in a first candidate region of the one or more first candidate regions. Additionally, one or more second candidate regions for the venous output function of the modified first imaging data can be determined that include a second blood vessel having at least the threshold diameter based on one or more second locations of second blood vessels having the threshold diameter in the modified atlas. The one or more second candidate regions include at least a portion of a sagittal sinus vein region or at least a portion of a straight sinus vein region. The venous output function can be determined based on second contrast agent concentration curves for second voxels included in a second candidate region of the one or more second candidate regions.

Further, the determination of values of perfusion parameters related to the first imaging data can be determined based on a tissue residue function for voxels included in one or more regions of the brain of the individual. The tissue residue function can be generated by performing one or more deconvolution operations with respect to contrast agent concentration curves of voxels included in the modified imaging data with respect to the arterial input function.

The one or more perfusion parameters can include relative cerebral blood volume that corresponds to an area under the tissue residue function for the individual voxel. The one or more perfusion parameters can also include relative cerebral blood flow that corresponds to a peak of the tissue residue function for the individual voxel. Additionally, the one or more perfusion parameters can include mean tracer transit time that corresponds to a ratio of the cerebral blood volume with respect to the cerebral blood flow for the individual voxel. In one or more examples, the one or more perfusion parameters can include $T_{max}$ that corresponds to a time of a peak of the tissue residue function for the individual voxel.

The process 700 can include, at operation 708, generating first overlay imaging data indicating the one or more first regions as a first overlay of the brain of the individual that corresponds to the first imaging data and in which a contrast agent is present. In one or more examples, the first overlay can be displayed over a slice of a perfusion-based computed tomography image.

At operation 710, the process 700 can include determining that tissue occurred in relation to one or more second regions of the brain of the individual. A portion of the one or more second regions can overlap with at least a portion of the one or more first regions. In various examples, a volume indicated by the second overlay can be greater than a volume indicated by the first overlay.

In one or more examples, damage to tissue that occurred in relation to the one or more second regions of the brain of the individual can be determined based on values of hypodensity with respect to the one or more second regions. The hypodensity values can be determined by analyzing intensity values of voxels included in the one or more second regions. To illustrate, a correlation can be determined between first voxels located in a first hemisphere of the brain of the individual and second voxels located in a second hemisphere of the brain of the individual. In addition, differences can be determined in first intensity values of individual first voxels with respect to second intensity values of individual second voxels. The individual second voxels can be contralaterally displayed with respect to the individual first voxels. The differences between the first intensity values and the second intensity values can indicate a measure of hypodensity of the brain tissue that corresponds to the individual first voxels and the individual second voxels.

In one or more implementations, measures of hypodensity can be generated by analyzing the differences with respect to a number of threshold intensity difference values to produce a number of groups of voxels with individual groups of voxels corresponding to one or more threshold intensity difference values of the number of threshold intensity difference values. The one or more threshold intensity difference values that correspond the individual groups of voxels can indicate a measure of hypodensity with respect to a respective portion of the brain tissue corresponding to the individual groups of voxels. In various examples, a first group of voxels can be determined that corresponds to at least a first threshold intensity difference value. The first group of voxels can correspond to a second region of the one or more second regions of the second overlay and the first group of voxels can correspond to a first measure of hypodensity of a first portion of the brain tissue. Additionally, a second group of voxels can be determined that corresponds to at least a second threshold intensity difference value. The second group of voxels can correspond to an additional second region of the one or more second regions of the second overlay. The second group of voxels can correspond to a second measure of hypodensity of a second portion of the brain tissue and the second measure of hypodensity can be different from the first level of hypodensity. In one or more illustrative examples, the different measures of hypodensity that correspond to different portions of brain tissue can be displayed in a manner that indicates the different threshold intensity difference values. For example, the first group of voxels can be displayed in conjunction with a first color and the second group of voxels can be displayed in conjunction with a second color.

The process 700 can also include, at operation 712, generating second overlay imaging data. The second overlay imaging data can indicate one or more regions of the brain of the individual as a second overlay to the second image of the brain of the individual. The second image can be a slice included in the second imaging data. Additionally, the second image can indicate that a contrast agent is absent from the brain of the individual.

Further, at operation 714, the process 700 can include generating an aggregate image that includes the first image of the brain of the individual, the first overlay, and the second overlay. In one or more illustrative examples, user interface data can be generated that corresponds to the user interface and provided to a computing device for display to a healthcare practitioner. The user interface can also display multiple slices included in the first imaging data. At least a portion of the individual slices can include a respective first overlay that corresponds to one or more regions of brain tissue displayed by the individual slice that have been damaged or that have at least a threshold probability of being damaged according to values of one or more perfusion parameters. Additionally, at least a portion of the individual slices can include a respective second overlay that corresponds to one or more regions of brain tissue displayed by the individual slice that have been damaged or that have at least the threshold probability of being damaged according to hypodensity values of the one or more regions.

FIG. 8 is a flowchart illustrating example operations of a process 800 to generate output images indicating damaged brain tissue based on onset of a biological condition corresponding to one or more vessels of brains of individuals, according to one or more example implementations. The process 800 can include, at operation 802, obtaining first imaging data of a brain of an individual. The first imaging data can be generated by a first imaging technique. The first imaging data can correspond to perfusion characteristics of fluid within the brain of the individual. At operation 804, the process 800 can also include obtaining second imaging data of the brain of the individual. The second imaging data can be generated by a second imaging technique that is a non-perfusion-based imaging modality. In one or more examples, the first imaging technique can implement one or more perfusion-based computed-tomography (CT) imaging techniques and the second imaging technique implements one or more non-contrast CT imaging techniques. In one or more additional examples, the first imaging technique implements one or more computed-tomography angiography (CTA) imaging techniques, and the second imaging technique implements one or more non-contrast CT imaging techniques. In one or more further examples, the first imaging data can be generated by an imaging technique that includes a non-perfusion-based imaging technique and the second imaging data can be generated by an additional imaging technique that includes a perfusion-based imaging technique.

In addition, at operation 806, the process 800 can include determining an amount of time elapsed since onset of a biological condition corresponding to one or more vessels of the brain of the individual. In one or more examples, the biological condition is a disruption of blood flow to at least one region of the brain of the individual. In one or more illustrative examples, the biological condition can comprise a stroke. The amount of time elapsed since onset of the biological condition can include a period of time from symptom onset with respect to the biological condition and a current time.

The process 800, at operation 808, can include determining, based on the first imaging data and the amount of time, one or more threshold levels of one or more blood flow parameters related to vessels of the brain of the individual. The one or more threshold levels can include a first threshold level of a blood flow parameter corresponding to a first period of time elapsed since onset of the biological condition. Additionally, the one or more threshold levels can include a second threshold of the blood flow parameter corresponding to a second period of time elapsed since onset of the biological condition. The second period of time can be greater than the first period of time. In various examples, the first period of time can be from 15 minutes to 2 hours or from 30 minutes to 4 hours. Further, the second period of time can be from 4 hours to 6 hours, from 3 hours to 5 hours, or from 5 hours to 8 hours. In one or more further examples, the second threshold level can correspond to a greater value of the blood flow parameter than the first threshold level. In one or more illustrative examples, the blood flow parameter can include cerebral blood flow.

Further, at operation 810, the process 800 can include determining that a blood flow parameter is at least the threshold level with respect to the brain of the individual. One or more values of the blood flow parameter can be determined by analyzing voxel information of the first imaging data. In one or more illustrative examples, the blood flow parameter can be analyzed with respect to the first threshold level during the first period of time. In these scenarios, damage to the region of the brain of the individual can be determined based on the blood flow parameter being at least the first threshold level. In addition, the blood flow parameter can also be analyzed with respect to the second threshold level during the second period of time. In these situations, damage to the region of the brain of the individual can be determined based on the blood flow parameter being at least the second threshold level. In one or more examples, the blood flow parameter can be analyzed during both the first period of time and the second period of time. In one or more additional examples, in situations where damage to the region of the brain of the individual is detected during the first period of time, a subsequent analysis during the second period of time may not take place. In one or more further examples, in scenarios where damage to the region of the brain of the individual is not detected during the first period of time, one or more subsequent analysis can take place, such as during the second period of time.

Additionally, the process 800, at operation 812, can include determining, based on the second imaging data, one or more measures of hypodensity with respect to the brain of the individual. The measures of hypodensity can be determined based on analyzing intensity values of voxels of the second imaging data. At operation 814, the process 800 can include determining, based on the one or more measures of hypodensity, that damage is present with respect to one or more regions of the brain of the individual. In various examples, values of intensity values of voxels of the second imaging data can be analyzed to determine the presence or absence of damaged brain tissue.

The process 800 can also, at operation 816, determining, based on the amount of time, a likelihood that the one or more measures of hypodensity correspond to tissue damage of the one or more regions. In one or more examples, the likelihood that the one or more measures of hypodensity correspond to tissue damage of the one or more regions may increase as the amount of time increases up to an upper limit on the amount of time. In various examples, the likelihood can be determined using one or more machine learning techniques. For example, one or more random forests models can be generated and executed to determine a likelihood that the one or more measures of hypodensity correspond to tissue damage of the one or more regions. In one or more illustrative examples, the likelihood can indicate a level of confidence that damage to the tissue is present in the one or more regions of the brain of the individual.

At operation 818, the process 800 can include generating an image indicating at least one region of the brain of the individual includes damaged tissue. In various examples, the image can include a perfusion-based image including one or more overlays. In one or more additional examples, the image can include a non-contrast CT image including one or more overlays. The one or more overlays can indicate a first region determined based on values of one or more perfusion parameters with respect to the threshold values. The one or more overlays can also indicate a second region determined based on the measures of hypodensity and the likelihood value. In one or more examples, the first region and the second region can at least partly overlap. Additionally, at least a portion of the first region may not comprise a portion of the second region. In one or more illustrative examples, the image can be one of a plurality of images that can be displayed that includes a perfusion-based image including at least one of the first overlay or the second overlay and a non-contrast CT image including at least one of the first overlay or the second overlay. In one or more further examples, one or more images can be generated indicating damage to tissue of the brain of the individual during a first period of time and indicating damage to tissue of the brain of the individual during a second period of time subsequent to the first period of time.

Figure 9:
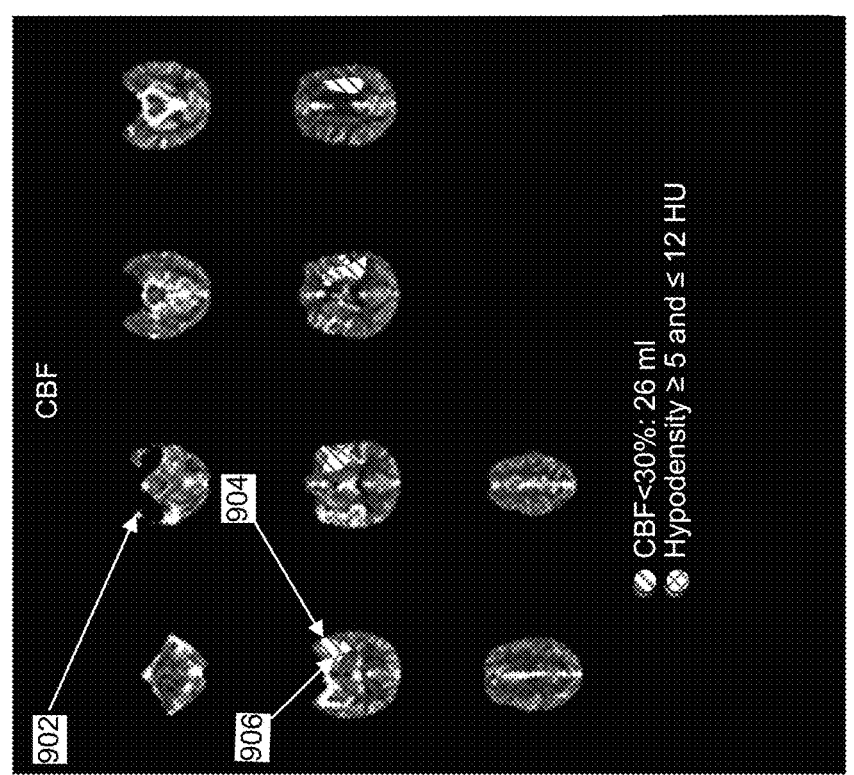
FIG. 9 is an illustration of an example user interface that includes a number of slices of a perfusion-based CT imaging data having overlays indicating regions of interest in the brain of an individual determined according to different perfusion parameters and according to a hypodensity analysis, according to one or more example implementations.

FIG. 9 is an example illustration of a user interface 900 that includes a number of slices of a perfusion-based CT image having overlays indicating regions of interest in the brain of an individual determined according to different perfusion parameters and according to a hypodensity analysis, according to one or more example implementations. For example, the user interface 900 can include a number of first slices 902. The number of first slices 902 can be captured using perfusion-based computed tomography imaging techniques and can correspond to different sections of the brain of an individual captured at different times. A portion of the number of first slices 902 can have a first overlay 904 that corresponds to a region of the brain of the individual having values of cerebral blood flow (CBF) less than a threshold value (30%). The threshold value can correspond to an amount of difference between the tissue included in the region associated with the first overlay 904 and cerebral blood flow values of healthy brain tissue.

A portion of the number of slices 902 can also include a second overlay 906. The second overlay can correspond to a region of the brain having hypodensity values within a threshold Hounsfield unit difference range (≥5 HU and ≤12 HU). The threshold difference range of voxels included in the region associated with the second overlay 906 can be in relation to contralaterally located voxels in a hemisphere of the brain that is disposed opposite the hemisphere of the brain that includes the regions associated with the first overlay 904 and the second overlay 906. In one or more illustrative examples, a combination of the volume related to the first overlay 904 and the volume related to the second overlay 906 can produce a total volume of damaged tissue in the brain of the individual.

Although the illustrative example of FIG. 9 shows the first overlay 904 and the second overlay 906 as regions having different patterns, in additional examples, the first overlay 904 and the second overlay 906 can be displayed using different colors, as a union of multiple colors, or in a manner where overlapping regions can be semi-opaque and be displayed as a mix of colors.

Figure 10:
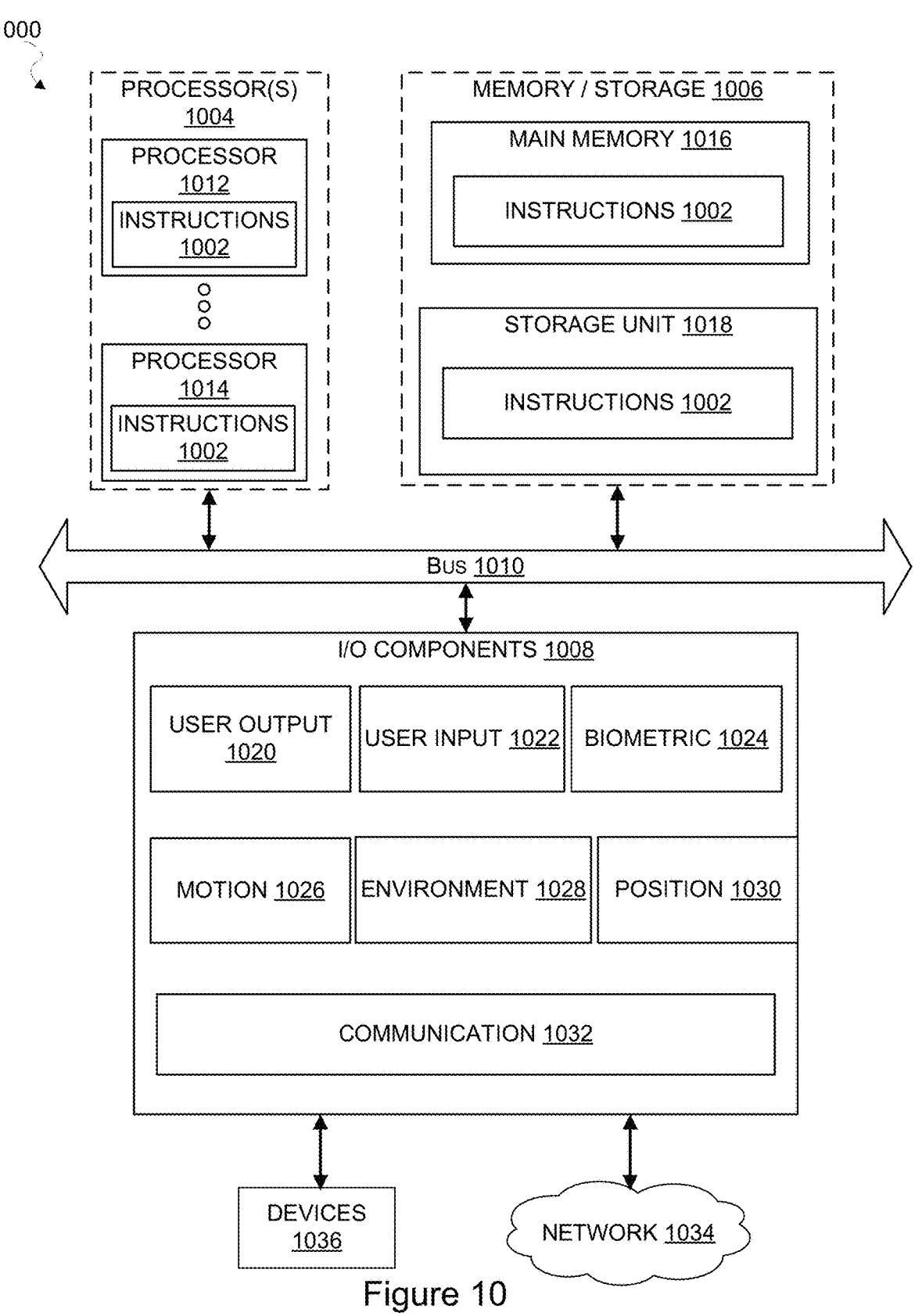
FIG. 10 is a block diagram illustrating components of a machine, in the form of a computer system, that may read and execute instructions from one or more machine-readable media to perform any one or more methodologies described herein, in accordance with one or more example implementations.

FIG. 10 is a block diagram illustrating components of a machine 1000, according to some example implementations, able to read instructions from a machine-readable medium (e.g., a machine-readable storage medium) and perform any one or more of the methodologies discussed herein. Specifically, FIG. 10 shows a diagrammatic representation of the machine 1000 in the example form of a computer system, within which instructions 1002 (e.g., software, a program, an application, an applet, an app, or other executable code) for causing the machine 1000 to perform any one or more of the methodologies discussed herein may be executed. As such, the instructions 1002 may be used to implement modules or components described herein. The instructions 1002 transform the general, non-programmed machine 1000 into a particular machine 1000 programmed to carry out the described and illustrated functions in the manner described. In alternative implementations, the machine 1000 operates as a standalone device or may be coupled (e.g., networked) to other machines. In a networked deployment, the machine 1000 may operate in the capacity of a server machine or a client machine in a server-client network environment, or as a peer machine in a peer-to-peer (or distributed) network environment. The machine 1000 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, at network switch, a network bridge, or any machine capable of executing the instructions 1002, sequentially or otherwise, that specify actions to be taken by machine 1000. Further, while only a single machine 1000 is illustrated, the term "machine" shall also be taken to include a collection of machines that individually or jointly execute the instructions 1002 to perform any one or more of the methodologies discussed herein.

The machine 1000 may include processors 1004, memory/storage 1006, and I/O components 1008, which may be configured to communicate with each other such as via a bus 1010. "Processor" in this context, refers to any circuit or virtual circuit (a physical circuit emulated by logic executing on an actual processor 1004) that manipulates data values according to control signals (e.g., "commands," "op codes," "machine code," etc.) and which produces corresponding output signals that are applied to operate a machine 1000. In an example implementation, the processors 1004 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1012 and a processor 1014 that may execute the instructions 1002. The term "processor" is intended to include multi-core processors 1004 that may comprise two or more independent processors (sometimes referred to as "cores") that may execute instructions 1002 contemporaneously. Although FIG. 10 shows multiple processors 1004, the machine 1000 may include a single processor 1012 with a single core, a single processor 1012 with multiple cores (e.g., a multi-core processor), multiple processors 1012, 1014 with a single core, multiple processors 1012, 1014 with multiple cores, or any combination thereof.

The memory/storage 1006 may include memory, such as a main memory 1016, or other memory storage, and a storage unit 1018, both accessible to the processors 1004 such as via the bus 1010. The storage unit 1018 and main memory 1016 store the instructions 1002 embodying any one or more of the methodologies or functions described herein. The instructions 1002 may also reside, completely or partially, within the main memory 1016, within the storage unit 1018, within at least one of the processors 1004 (e.g., within the processor's cache memory), or any suitable combination thereof, during execution thereof by the machine 1000. Accordingly, the main memory 1016, the storage unit 1018, and the memory of processors 1004 are examples of machine-readable media. "Machine-readable media," also referred to herein as "computer-readable storage media", in this context, refers to a component, device, or other tangible media able to store instructions 1002 and data temporarily or permanently and may include, but is not limited to, random-access memory (RAM), read-only memory (ROM), buffer memory, flash memory, optical media, magnetic media, cache memory, other types of storage (e.g., erasable programmable read-only memory (EEPROM)) and/or any suitable combination thereof. The term "machine-readable medium" may be taken to include a single medium or multiple media (e.g., a centralized or distributed database, or associated caches and servers) able to store instructions 1002. The term "machine-readable medium" shall also be taken to include any medium, or combination of multiple media, that is capable of storing instructions 1002 (e.g., code) for execution by a machine 1000, such that the instructions 1002, when executed by one or more processors 1004 of the machine 1000, cause the machine 1000 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1008 may include a wide variety of components to receive input, provide output, produce output, transmit information, exchange information, capture measurements, and so on. The specific I/O components 1008 that are included in a particular machine 1000 will depend on the type of machine. For example, portable machines such as mobile phones will likely include a touch input device or other such input mechanisms, while a headless server machine will likely not include such a touch input device. It will be appreciated that the I/O components 1008 may include many other components that are not shown in FIG. 10. The I/O components 1008 are grouped according to functionality merely for simplifying the following discussion and the grouping is in no way limiting. In various example implementations, the I/O components 1008 may include user output components 1020 and user input components 1022. The user output components 1020 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1022 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like.

In further example implementations, the I/O components 1008 may include biometric components 1024, motion components 1026, environmental components 1028, or position components 1030 among a wide array of other components. For example, the biometric components 1024 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1026 may include acceleration sensor components (e.g., accelerometer), gravitation sensor components, rotation sensor components (e.g., gyroscope), and so forth. The environmental components 1028 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1030 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1008 may include communication components 1032 operable to couple the machine 1000 to a network 1034 or devices 1036. For example, the communication components 1032 may include a network interface component or other suitable device to interface with the network 1034. In further examples, communication components 1032 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 1036 may be another machine 1000 or any of a wide variety of peripheral devices (e.g., a peripheral device coupled via a USB).

Moreover, the communication components 1032 may detect identifiers or include components operable to detect identifiers. For example, the communication components 1032 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1032, such as location via Internet Protocol (IP) geo-location, location via Wi-Fi® signal triangulation, location via detecting an NFC beacon signal that may indicate a particular location, and so forth.

"Component," in this context, refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example implementations, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an ASIC. A hardware component may also include programmable logic or circuitry that is temporarily configured by software to perform certain operations. For example, a hardware component may include software executed by a general-purpose processor 1004 or other programmable processor. Once configured by such software, hardware components become specific machines (or specific components of a machine 1000) uniquely tailored to perform the configured functions and are no longer general-purpose processors 1004. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering implementations in which hardware components are temporarily configured (e.g., programmed), each of the hardware components need not be configured or instantiated at any one instance in time. For example, where a hardware component comprises a general-purpose processor 1004 configured by software to become a special-purpose processor, the general-purpose processor 1004 may be configured as respectively different special-purpose processors (e.g., comprising different hardware components) at different times. Software accordingly configures a particular processor 1012, 1014 or processors 1004, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In implementations in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors 1004 that are temporarily configured (e.g., by software) or permanently configured to perform the relevant operations. Whether temporarily or permanently configured, such processors 1004 may constitute processor-implemented components that operate to perform one or more operations or functions described herein. As used herein, "processor-implemented component" refers to a hardware component implemented using one or more processors 1004. Similarly, the methods described herein may be at least partially processor-implemented, with a particular processor 1012, 1014 or processors 1004 being an example of hardware. For example, at least some of the operations of a method may be performed by one or more processors 1004 or processor-implemented components. Moreover, the one or more processors 1004 may also operate to support performance of the relevant operations in a "cloud computing" environment or as a "software as a service" (SaaS). For example, at least some of the operations may be performed by a group of computers (as examples of machines 1000 including processors 1004), with these operations being accessible via a network 1034 (e.g., the Internet) and via one or more appropriate interfaces (e.g., an API). The performance of certain of the operations may be distributed among the processors, not only residing within a single machine 1000, but deployed across a number of machines. In some example implementations, the processors 1004 or processor-implemented components may be located in a single geographic location (e.g., within a home environment, an office environment, or a server farm). In other example implementations, the processors 1004 or processor-implemented components may be distributed across a number of geographic locations.

Figure 11:
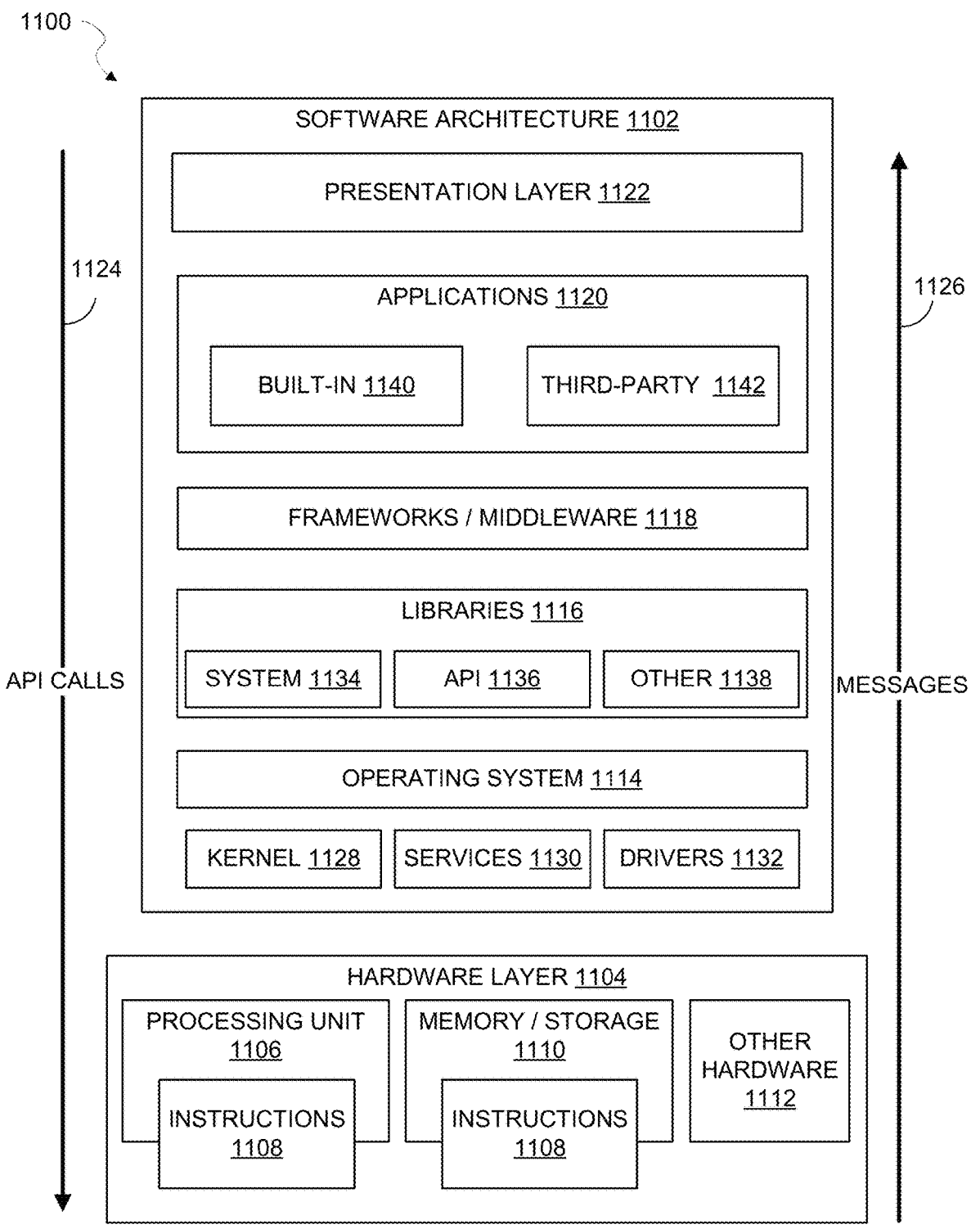
FIG. 11 is block diagram illustrating a representative software architecture that may be used in conjunction with one or more hardware architectures described herein, in accordance with one or more example implementations.

FIG. 11 is a block diagram illustrating system 1100 that includes an example software architecture 1102, which may be used in conjunction with various hardware architectures herein described. FIG. 11 is a non-limiting example of a software architecture and it will be appreciated that many other architectures may be implemented to facilitate the functionality described herein. The software architecture 1102 may execute on hardware such as machine 1000 of FIG. 10 that includes, among other things, processors 1004, memory/storage 1006, and input/output (I/O) components 1008. A representative hardware layer 1104 is illustrated and can represent, for example, the machine 1000 of FIG. 10. The representative hardware layer 1104 includes a processing unit 1106 having associated executable instructions 1108. Executable instructions 1108 represent the executable instructions of the software architecture 1102, including implementation of the methods, components, and so forth described herein. The hardware layer 1104 also includes at least one of memory or storage modules memory/storage 1110, which also have executable instructions 1108. The hardware layer 1104 may also comprise other hardware 1112.

In the example architecture of FIG. 11, the software architecture 1102 may be conceptualized as a stack of layers where each layer provides particular functionality. For example, the software architecture 1102 may include layers such as an operating system 1114, libraries 1116, frameworks/middleware 1118, applications 1120, and a presentation layer 1122. Operationally, the applications 1120 or other components within the layers may invoke API calls 1124 through the software stack and receive messages 1126 in response to the API calls 1124. The layers illustrated are representative in nature and not all software architectures have all layers. For example, some mobile or special purpose operating systems may not provide a frameworks/middleware 1118, while others may provide such a layer. Other software architectures may include additional or different layers.

The operating system 1114 may manage hardware resources and provide common services. The operating system 1114 may include, for example, a kernel 1128, services 1130, and drivers 1132. The kernel 1128 may act as an abstraction layer between the hardware and the other software layers. For example, the kernel 1128 may be responsible for memory management, processor management (e.g., scheduling), component management, networking, security settings, and so on. The services 1130 may provide other common services for the other software layers. The drivers 1132 are responsible for controlling or interfacing with the underlying hardware. For instance, the drivers

1132 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1116 provide a common infrastructure that is used by at least one of the applications 1120, other components, or layers. The libraries 1116 provide functionality that allows other software components to perform tasks in an easier fashion than to interface directly with the underlying operating system 1114 functionality (e.g., kernel 1128, services 1130, drivers 1132). The libraries 1116 may include system libraries 1134 (e.g., C standard library) that may provide functions such as memory allocation functions, string manipulation functions, mathematical functions, and the like. In addition, the libraries 1116 may include API libraries 1136 such as media libraries (e.g., libraries to support presentation and manipulation of various media format such as MPEG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 1116 may also include a wide variety of other libraries 1138 to provide many other APIs to the applications 1120 and other software components/modules.

The frameworks/middleware 1118 (also sometimes referred to as middleware) provide a higher-level common infrastructure that may be used by the applications 1120 or other software components/modules. For example, the frameworks/middleware 1118 may provide various graphical user interface functions, high-level resource management, high-level location services, and so forth. The frameworks/middleware 1118 may provide a broad spectrum of other APIs that may be utilized by the applications 1120 or other software components/modules, some of which may be specific to a particular operating system 1114 or platform.

The applications 1120 include built-in applications 1140 and third-party applications 1142. Examples of representative built-in applications 1140 may include, but are not limited to, a contacts application, a browser application, a book reader application, a location application, a media application, a messaging application, or a game application. Third-party applications 1142 may include an application developed using the ANDROID™ or IOS™ software development kit (SDK) by an entity other than the vendor of the particular platform, and may be mobile software running on a mobile operating system such as IOS™ ANDROID™, WINDOWS® Phone, or other mobile operating systems. The third-party applications 1142 may invoke the API calls 1124 provided by the mobile operating system (such as operating system 1114) to facilitate functionality described herein.

The applications 1120 may use built-in operating system functions (e.g., kernel 1128, services 1130, drivers 1132), libraries 1116, and frameworks/middleware 1118 to create UIs to interact with users of the system. Alternatively, or additionally, in some systems, interactions with a user may occur through a presentation layer, such as presentation layer 1122. In these systems, the application/component "logic" can be separated from the aspects of the application/component that interact with a user.

Changes and modifications may be made to the disclosed implementations without departing from the scope of the present disclosure. These and other changes or modifications are intended to be included within the scope of the present disclosure, as expressed in the following claims.

What is claimed is:

1. A method comprising:

obtaining, by a computing system including one or more computing devices that each include a processor and memory, imaging data that indicates characteristics within a brain of and individual based on a presence of a contrast agent within the brain of the individual;

determining, by the computing system, an amount of time elapsed since onset of a biological condition corresponding to one or more vessels of the brain of the individual;

determining, by the computing system, a plurality of threshold levels of one or more blood flow parameters including a first threshold level of the one or more blood flow parameters corresponding to a first period of time since the onset of the biological condition and a second threshold level of the one or more blood flow parameters corresponding to a second period of time since the onset of the biological condition;

in response to determining, by the computing system and based on the imaging data, that the amount of time elapsed since the onset of the biological condition corresponds to the first period of time, determining that the first threshold level is applied to the one or more blood flow parameters, wherein the one or more blood flow parameters are determined based on the imaging data;

determining, by the computing system, that a blood flow parameter of the one or more blood flow parameters corresponds to the first threshold level with respect to a vessel of the brain of the individual; and generating, by the computing system and based on the blood flow parameter, an image indicating at least one region of the brain of the individual that includes damaged tissue.

2. The method of claim 1, wherein the imaging data is obtained by implementing one or more perfusion-based computed-tomography (CT) imaging techniques.

3. The method of claim 2, wherein the blood flow parameter includes cerebral blood flow.

4. The method of claim 1, wherein the imaging data is obtained by implementing one or more computed tomography angiography (CTA) imaging techniques.

5. The method of claim 1, wherein the second threshold level corresponds to a greater value of the blood flow parameter than the first threshold level.

6. The method of claim 1, comprising:

analyzing, by the computing system, voxel information of the imaging data to determine the blood flow parameter.

7. The method of claim 1, comprising:

obtaining, by the computing system, additional imaging data that indicates additional characteristics within the brain of the individual in an absence of the contrast agent within the brain of the individual; and analyzing, by the computing system, intensity values of a number of voxels of the additional imaging data to determine one or more measures of hypodensity.

8. The method of claim 7, comprising:

determining, by the computing system based on the one or more measures of hypodensity, that damage is present with respect to tissue of one or more regions of the brain of the individual; and determining, by the computing system and based on the amount of time, a likelihood that the one or more measures of hypodensity correspond to tissue damage of the one or more regions.

9. The method of claim 8, comprising:

determining, by the computing system, that a blood flow parameter of the one or more blood flow parameters has a value of at least the first threshold level with respect to a blood vessel included in a first region of the brain of the individual;

determining, by the computing system and based on the likelihood, that tissue damage has occurred with respect to a second region of the brain of the individual; and generating, by the computing system, user interface data corresponding to a user interface including a first overlay indicating the first region of the brain of the individual and a second overlay indicating the second region of the brain of the individual.

10. The method of claim 1, wherein the biological condition is a disruption of blood flow to at least one region of the brain of the individual.

11. A system comprising:

one or more hardware processors; and one or more non-transitory computer-readable storage media including computer-readable instructions that, when executed by the one or more hardware processors, cause the one or more hardware processors to perform operations comprising:

obtaining imaging data that indicates characteristics within a brain of an individual based on a presence of a contrast agent within the brain of the individual;

determining an amount of time elapsed since onset of a biological condition corresponding to one or more vessels of the brain of the individual;

determining a plurality of threshold levels of one or more blood flow parameters including a first threshold level of the one or more blood flow parameters corresponding to a first period of time since the onset of the biological condition and a second threshold level of the one or more blood flow parameters corresponding to a second period of time since the onset of the biological condition;

in response to determining, based on the imaging data, that the amount of time elapsed since the onset of the biological condition corresponds to the first period of time, determining that the first threshold level is applied to the one or more blood flow parameters, wherein the one or more blood flow parameters are determined based on the imaging data determining that a blood flow parameter of the one or more blood flow parameters corresponds to the first threshold level with respect to a vessel of the brain of the individual; and generating, based on the vessel of the brain of the individual, an image indicating at least one region of the brain of the individual that includes damaged tissue.

12. The system of claim 11, wherein the one or more non-transitory computer-readable storage media include additional computer-readable instructions that, when executed by the one or more hardware processors, cause the one or more hardware processors to perform additional operations comprising:

obtaining additional imaging data that indicates additional characteristics within the brain of the individual in an absence of the contrast agent within the brain of the individual; and analyzing intensity values of a number of voxels of the additional imaging data to determine one or more measures of hypodensity.

13. The system of claim 12, wherein the imaging data is obtained by implementing one or more perfusion-based computed-tomography (CT) imaging techniques and the additional imaging data is obtained by implementing one or more non-contrast CT imaging techniques.

14. The system of claim 12, wherein the imaging data is obtained by implementing one or more computed-tomography angiography (CTA) imaging techniques and the additional imaging data is obtained by implementing one or more non-contrast CT imaging techniques.

15. The system of claim 12, wherein the one or more non-transitory computer-readable storage media include additional computer-readable instructions that, when executed by the one or more hardware processors, cause the one or more hardware processors to perform additional operations comprising:

generating an image that includes a first overlay corresponding to the at least one region of the brain of the individual and a second overlay corresponding to an additional region of the brain of the individual.

16. A method comprising:

obtaining, by a computing system including one or more computing devices that each include a processor and memory, imaging data that indicates second characteristics within a brain of an individual in the absence of a contrast agent within the brain of the individual;

determining, by the computing system, an amount of time elapsed since onset of a biological condition corresponding to one or more vessels of the brain of the individual;

analyzing, by the computing system, intensity values of a number of voxels of the imaging data to determine one or more measures of hypodensity;

determining, by the computing system based on the one or more measures of hypodensity, that damage is present with respect to tissue of one or more regions of the brain of the individual;

determining, by the computing system and based on the amount of time, a likelihood that the one or more measures of hypodensity correspond to tissue damage of the one or more regions; and generating, by the computing system and based on the likelihood, an image indicating at least one region of the brain of the individual that includes damaged tissue.

17. The method of claim 16, comprising:

obtaining, by the computing system, additional imaging data that indicates additional characteristics within the brain of the individual based on a presence of a contrast agent within the brain of the individual; and determining, by the computing system and based on the amount of time, one or more threshold levels of one or more blood flow parameters related to vessels of the brain of the individual, the one or more threshold levels indicating damage to brain of the individual.

18. The method of claim 17, comprising:

determining, by the computing system and based on the amount of time, one or more threshold levels of one or more blood flow parameters related to vessels of the brain of the individual, the one or more threshold levels indicating damage to brain of the individual; and determining, by the computing system, that a blood flow parameter of the one or more blood flow parameters is at least a threshold level of the one or more threshold levels with respect to a vessel of the brain of the individual.

19. The method of claim 18, comprising:

generating, by the computing system, first user interface data corresponding to one or more first values of a blood flow parameter of the one or more blood flow parameters and one or more first measures of hypodensity calculated with respect to a first period of time; and generating, by the computing system, second user interface data corresponding to one or more second values of the blood flow parameter and one or more second measures of hypodensity calculated with respect to a second period of time.

20. The method of claim 17, wherein:

the imaging data is generated by an imaging technique that includes a non-perfusion-based imaging technique; and the additional imaging data is generated by an additional imaging technique that includes a perfusion-based imaging technique.

\* \* \* \* \*